United States Patent
Kitano et al.

(10) Patent No.: US 8,465,416 B2
(45) Date of Patent: Jun. 18, 2013

(54) ENDOSCOPE

(75) Inventors: Seiji Kitano, Akishima (JP); Hidenobu Kimura, Hachioji (JP); Kotaro Yoda, Kiyose (JP); Takayasu Miyagi, Hachioji (JP); Haruhiko Kaiya, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 363 days.

(21) Appl. No.: 12/704,629

(22) Filed: Feb. 12, 2010

(65) Prior Publication Data

US 2010/0145144 A1    Jun. 10, 2010

Related U.S. Application Data

(62) Division of application No. 11/799,696, filed on May 2, 2007, now abandoned.

(30) Foreign Application Priority Data

May 17, 2006  (JP) ................................. 2006-138302
Aug. 30, 2006  (JP) ................................. 2006-234520

(51) Int. Cl.
  *A61B 1/00*   (2006.01)
(52) U.S. Cl.
  USPC ............................ 600/107; 600/104; 600/106
(58) Field of Classification Search
  CPC ...... A61B 1/012; A61B 1/018; A61B 1/00087; A61B 1/00098
  USPC ................ 600/104, 106, 107, 114, 127, 129, 600/153
  See application file for complete search history.

(56) References Cited

U.S. PATENT DOCUMENTS

| 4,407,273 | A  | * | 10/1983 | Ouchi | 600/107 |
|---|---|---|---|---|---|
| 4,452,236 | A  | * | 6/1984 | Utsugi | 600/107 |
| 7,087,010 | B2 |  | 8/2006 | Ootawara et al. | |
| 2002/0087100 | A1 | * | 7/2002 | Onuki et al. | 600/585 |
| 2002/0091303 | A1 |  | 7/2002 | Ootawara et al. | |
| 2003/0073955 | A1 | * | 4/2003 | Otawara | 604/164.01 |
| 2004/0049095 | A1 | * | 3/2004 | Goto et al. | 600/107 |
| 2005/0049455 | A1 | * | 3/2005 | Ootawara et al. | 600/107 |
| 2006/0235271 | A1 | * | 10/2006 | Carter et al. | 600/107 |
| 2007/0208219 | A1 | * | 9/2007 | Carter | 600/107 |
| 2007/0249898 | A1 | * | 10/2007 | Otawara | 600/107 |

FOREIGN PATENT DOCUMENTS

| AU | 2005258423 A1 | | 1/2006 |
|---|---|---|---|
| JP | 2002-034905 | | 2/2002 |
| JP | 2005-304586 | | 11/2005 |
| JP | 2006-15017 | | 1/2006 |
| JP | 2006020725 A | * | 1/2006 |

* cited by examiner

Primary Examiner — Matthew J Kasztejna
Assistant Examiner — Ryan Henderson
(74) Attorney, Agent, or Firm — Scully, Scott, Murphy & Presser, P.C.

(57) ABSTRACT

An endoscope includes: a treatment instrument elevator base including a contact surface which contacts with a treatment instrument inserted into a treatment instrument insertion channel, and rotatably provided to a distal end to elevate the instrument; a contact portion provided to the distal end to contact with the instrument when the elevator base is elevated; a first leading portion provided to the contact surface to lead the instrument to a predetermined position on the contact surface as the elevator base is rotated; a holding portion provided to the contact surface and the contact portion, and including a grasping surface for sandwiching the instrument with a diameter not exceeding a predetermined value; and a second leading portion provided to the contact portion to lead the instrument larger than the grasping surface away from the holding portion.

6 Claims, 27 Drawing Sheets

36  37  38

36  37  38   B

ENDOSCOPE

CROSS REFERENCE TO RELATED APPLICATION

This application is a divisional application of U.S. Ser. No. 11/799,696 filed on May 2, 2007 and claims benefit of Japanese Application No. 2006-138302 filed on May 17, 2006 and No. 2006-234520 filed on Aug. 30, 2006 the entire contents of which are incorporated by this reference.

BACKGROUND OF THE INVENTION

1. Field of the Invention

The present invention relates to an endoscope, and particularly to an endoscope suitable for performing an operation of exchanging treatment instruments by using a guide wire in an endoscopy and an endoscopic operation of the pancreaticobiliary duct system.

2. Description of the Related Art

In recent years, an endoscopic treatment using an endoscope has been increasingly performed in the treatment of a disease in the digestive tract system and the pancreaticobiliary duct system. The existing treatments of the pancreaticobiliary duct system using an endoscope include a diagnostic treatment of performing endoscopic cholangiography and pancreatography and also a therapeutic treatment of removing a gallstone located in the common bile duct or the like by using a balloon or a grasping treatment instrument.

In performing an endoscopic treatment of a pancreatic duct, a bile duct, a hepatic duct, or the like by using an endoscope, a surgeon usually and commonly inserts the distal end of an insertion portion of the endoscope into a position in the vicinity of the duodenal papilla, and then selectively inserts a treatment instrument, such as a catheter, into the pancreatic duct or the bile duct while using a guide wire as a guide under X-ray illumination.

In such an endoscopy and an endoscopic operation of the pancreaticobiliary duct system, the guide wire is inserted in the treatment instrument, when the treatment instrument, such as a catheter, is inserted into a treatment instrument insertion channel of the endoscope to be used in the observation or treatment of the pancreaticobiliary duct system with the endoscope.

Therefore, the guide wire is moved in conjunction with the movement of the treatment instrument with respect to the endoscope. Thus, to exchange the treatment instrument with another treatment instrument by using the guide wire as a guide while keeping the distal end of the guide wire inserted in the papilla, for example, the guide wire needs to be held within the distal end of the insertion portion to keep the distal end of the guide wire inserted in the papilla.

In light of the above need, there is an endoscope according to a conventional technique, the insertion portion of which includes guide wire fixing means for unlockably locking the guide wire, as disclosed in Japanese Unexamined Patent Application Publication No. 2002-034905, for example.

The endoscope of Japanese Unexamined Patent Application Publication No. 2002-034905 includes an operation portion connected to the proximal end of the insertion portion, and a treatment instrument elevator base provided in the distal end of the insertion portion and operable by the operation of the operation portion. The endoscope is configured such that a top portion of a leading surface of the treatment instrument elevator base is provided with a slit which functions as the guide wire fixing means for making only the guide wire engageable when the guide wire is elevated through the operation of the treatment instrument elevator base by the operation portion.

According to the thus configured endoscope apparatus, in the observation or treatment of the pancreaticobiliary duct system using the endoscope, as the treatment instrument elevator base is elevated, the guide wire is pressed into and engaged with a substantially V-shaped slit (a wire locking groove) provided in a bottom portion of the treatment instrument elevator base due to the reaction force of the guide wire itself inserted in the papilla, and is pressed against a substantially planar upper surface of a rigid distal end body. Thereby, the guide wire is mechanically fixed.

Further, the endoscope provided with the treatment instrument elevator base in the distal end thereof includes an endoscope in which the treatment instrument elevator base is elevated by a drive arm provided inside a side surface of the distal end to prevent such inconvenience as interference of the projected treatment instrument, such as the guide wire, with an elevator wire or the like, as disclosed in Japanese Unexamined Patent Application Publication No. 2005-304586, for example.

SUMMARY OF THE INVENTION

An endoscope according to a first aspect of the present invention includes an insertion portion, a treatment instrument insertion channel, a treatment instrument elevator base, a contact portion, a first leading portion, a holding portion, and a second leading portion. The insertion portion includes a distal end on a distal end side thereof, and is inserted into a body cavity. The treatment instrument insertion channel is disposed in the insertion portion, and communicates with the distal end. The treatment instrument elevator base includes a contact surface which comes in contact with a treatment instrument inserted into the treatment instrument insertion channel. Further, the treatment instrument elevator base is rotatably provided to the distal end to elevate the treatment instrument through the contact of the contact surface with the treatment instrument in accordance with the operation of an operation portion. The contact portion is provided to the distal end to be contactable with the treatment instrument when the treatment instrument elevator base is elevated. The first leading portion is provided to the contact surface of the treatment instrument elevator base to lead the treatment instrument to a predetermined position on the contact surface in accordance with a rotating movement of the treatment instrument elevator base. The holding portion is provided to the contact surface and the contact portion, and includes a grasping surface of a predetermined size for sandwiching, between the contact surface and the contact portion, the treatment instrument led by the first leading portion, the treatment instrument having a diameter not exceeding a predetermined value. The second leading portion is provided to the contact portion to lead and hold the treatment instrument in a direction away from the holding portion, the treatment instrument being larger in size than the grasping surface of the holding portion.

An endoscope according to a second aspect of the present invention includes an insertion portion, a treatment instrument insertion channel, a treatment instrument elevator base, a contact portion, a leading portion, and a holding fixture portion. The insertion portion includes a distal end on a distal end side thereof, and is inserted into a body cavity. The treatment instrument insertion channel is disposed in the insertion portion, and communicates with the distal end. The treatment instrument elevator base includes a contact surface which comes in contact with a treatment instrument inserted into the treatment instrument insertion channel, and is rotatably provided to the distal end to elevate the treatment instrument through the contact of the contact surface with the treatment instrument in accordance with the operation of an operation portion. The contact portion is provided to the distal end to be contactable with the treatment instrument when the treatment instrument elevator base is elevated. The leading portion leads the treatment instrument to a predetermined position on the contact portion in accordance with a rotating movement of the treatment instrument elevator base. The holding fixture portion is provided to the contact surface and the contact portion, and includes a grasping surface for sandwiching, between the contact surface and the contact portion, the treatment instrument led by the leading portion, the treatment instrument having a diameter not exceeding a predetermined value.

An endoscope according to a third aspect of the present invention includes an insertion portion, a treatment instrument insertion channel, a treatment instrument elevator base, a fixing member, a first treatment instrument holding portion, a second treatment instrument holding portion, a holding fixture portion, and a leading portion. The insertion portion includes a distal end on a distal end side thereof, and is inserted into a body cavity. The treatment instrument insertion channel is disposed in the insertion portion, and communicates with the distal end. The treatment instrument elevator base is rotatably provided to the distal end to elevate a first treatment instrument or a second treatment instrument inserted into the treatment instrument insertion channel, in accordance with the operation of an operation portion. The fixing member is disposed to the distal end, and functions as a fulcrum when the treatment instrument elevator base is actuated to change the direction of the first treatment instrument or the second treatment instrument. The first treatment instrument holding portion is provided to the treatment instrument elevator base to hold, at a first position, the first treatment instrument inserted into the treatment instrument insertion channel. The second treatment instrument holding portion is provided to the treatment instrument elevator base to hold, at a second position different from the first position, the second treatment instrument inserted into the treatment instrument insertion channel. The holding fixture portion is provided to each of the treatment instrument elevator base and the fixing member to sandwich, between the treatment instrument elevator base and the fixing member, the first treatment instrument elevated by the treatment instrument elevator base. The leading portion is provided to the fixing member to lead the first treatment instrument elevated in accordance with a rotating movement of the treatment instrument elevator base to the holding fixture portion of the fixing member, without leading the second treatment instrument elevated in accordance with the rotating movement of the treatment instrument elevator base to the holding fixture portion.

The above and other objects, features and advantages of the invention will become more clearly understood from the following description referring to the accompanying drawings.

DETAILED DESCRIPTION OF THE PREFERRED EMBODIMENTS

Embodiments of the present invention will be described below with reference to the drawings.

First Embodiment

Figure 1:
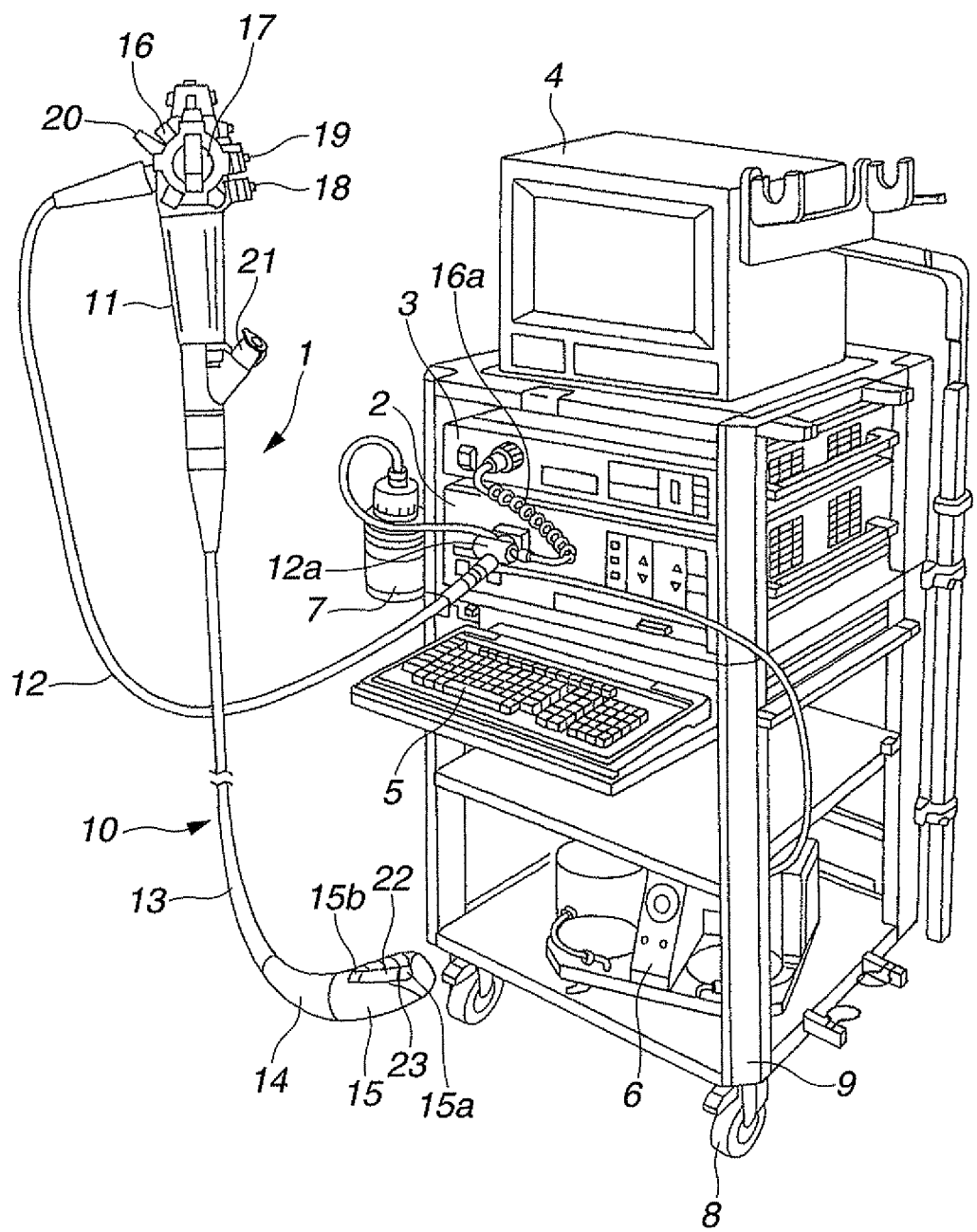
FIG. 1 is a perspective view according to a first embodiment of the present invention, illustrating a schematic configuration of the entire system of an endoscope apparatus incorporating an endoscope and a variety of external devices.
Figure 2:
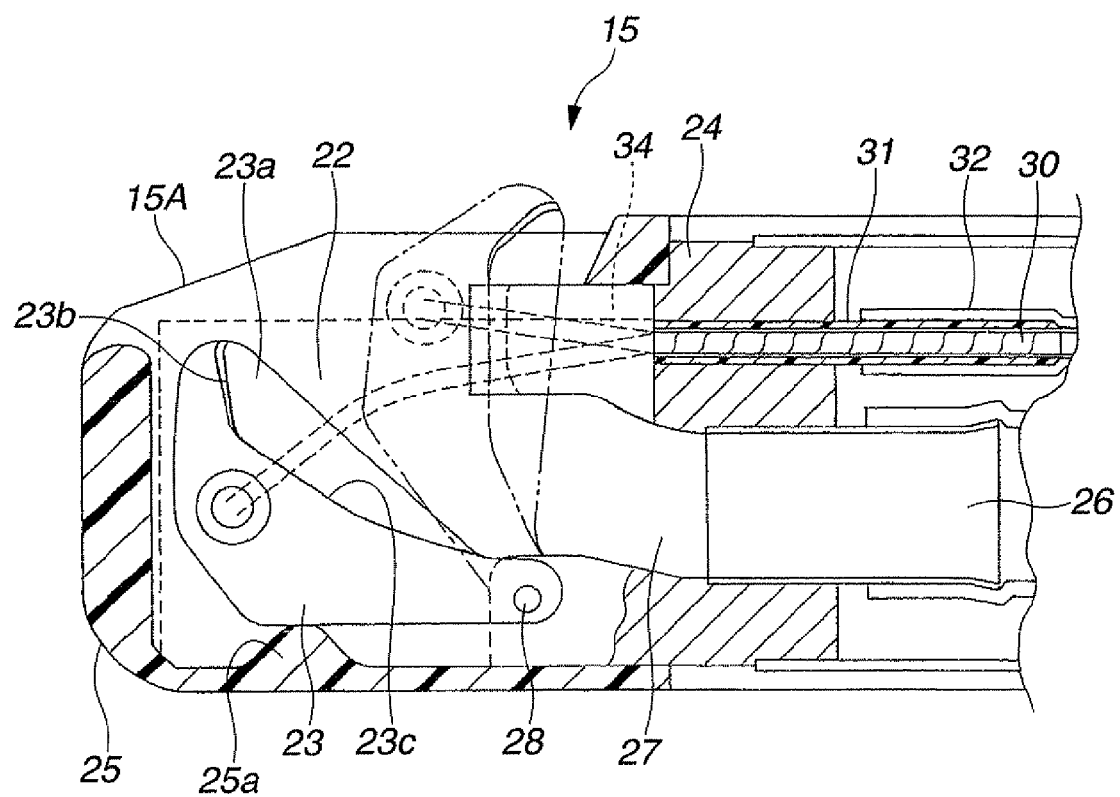
FIG. 2 is a vertical cross-sectional view of essential parts according to the first embodiment of the present invention, illustrating an internal configuration of a distal end of an insertion portion of the endoscope.
Figure 3:
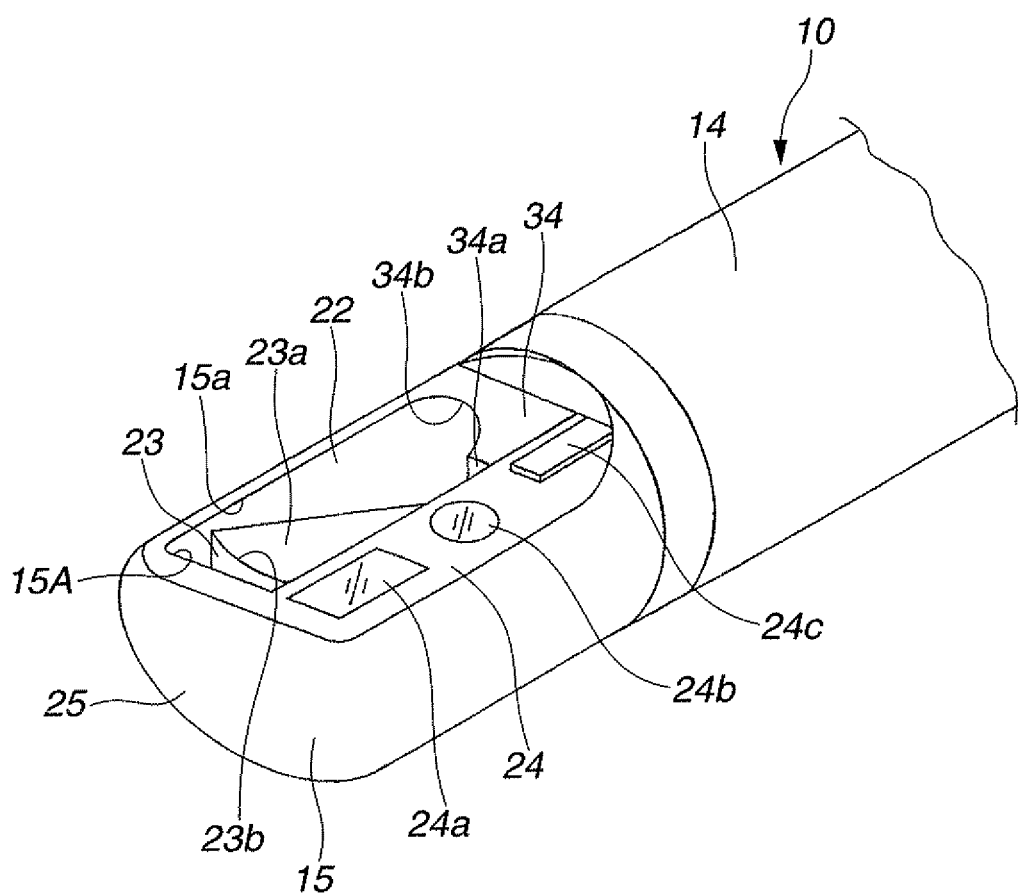
FIG. 3 is a perspective view according to the first embodiment of the present invention, illustrating an external configuration of the distal end including a treatment instrument holding mechanism.

FIGS. 1 to 14 illustrate a first embodiment of the present invention. FIG. 1 is a perspective view according to the first embodiment, illustrating a schematic configuration of the entire system of an endoscope apparatus incorporating an endoscope and a variety of external devices. FIG. 2 is a vertical cross-sectional view of essential parts, illustrating an internal configuration of a distal end of an insertion portion of the endoscope. FIG. 3 is a perspective view illustrating an external configuration of the distal end including a treatment instrument holding mechanism.

As illustrated in FIG. 1, an endoscope 1 of the first embodiment is configured to form an endoscope system in combination with an equipment group including external devices of a light source device 2, an image processor 3, a monitor 4, an input keyboard 5, a suction pump device 6, and a water supply tank 7, for example. The above equipments are placed on a rack 9 equipped with carriers 8.

The endoscope 1 is configured to include an elongated insertion portion 10 inserted into a body cavity, an operation portion 11 provided on the proximal side and connected to the proximal end of the insertion portion 10, and a universal cord 12, the proximal end of which is connected to the operation portion 11.

The insertion portion 10 is configured to include an elongated flexible tube portion 13 having flexibility, a bending portion 14 connected to the distal end of the flexible tube portion 13, and a rigid distal end 15 provided consecutively to the bending portion 14 and disposed at the most distal end position of the insertion portion 10.

Further, the distal end of the universal cord 12 connected to the operation portion 11 is provided with a connector 12a. The connector 12a is provided with a light guide connector portion and an electric contact portion, and is connected to the light source device 2, which is one of the external devices.

The connector 12a is also connected to the image processor 3 through a signal cable 16a, which is connected to an internal signal line.

The outer circumferential surface of the distal end 15 of the endoscope 1 is formed with a concave cutout portion 15a having a cutout side surface. On one side of the side portion of the cutout portion 15a, a channel opening 15A (see FIG. 2) is disposed. Further, beside the channel opening 15A, an illumination lens (an illumination window) 24a forming an illumination optical system and an objective lens (an observation lens) 24b forming an observation optical system are juxtaposed, as illustrated in FIG. 3.

Further, a rear end wall surface 15b of the cutout portion 15a of the distal end 15 is provided with a nozzle 24c projecting from the rear end wall surface 15b to supply air and water. The nozzle 24c is used to spray fluid, such as water and air, onto the outer surface of the objective lens 24b for cleaning the lens surface.

Although not illustrated, the illumination lens 24a is connected to a light guide functioning as an optical transmission path. The inside of the objective lens 24b is disposed with a CCD (Charge Coupled Device), which is an image pickup device forming the observation optical system. The CCD is connected to a circuit board for extracting an image signal.

The not-illustrated light guide, CCD, and circuit board described above are disposed in a storage portion formed in a rigid distal end portion 24, which forms a distal end body in the distal end 15.

The operation portion 11 of the endoscope 1 is provided with a bending operation portion 17 for bending the bending portion 14 of the insertion portion 10 in the vertical or lateral direction, an air and water supply button 18, and a suction operation button 19. Further, the proximal end of the operation portion 11 is provided with an insertion opening 21 which communicates with a treatment instrument insertion channel 26 (see FIG. 2).

Through the operation of the air and water supply button 18, a surgeon can cause the nozzle 24c of the distal end 15 to selectively squirt gas and liquid. Further, through the operation of the suction operation button 19, the surgeon can selectively generate suction force in the channel opening 15A of the distal end 15 through the treatment instrument insertion channel 26 to thereby remove mucus and so forth present in the body cavity.

Although not illustrated, the operation portion 11 includes therein an elevator base actuating mechanism (not illustrated) for operating an elevator wire 30 connected to a treatment instrument elevator base 23. The elevator base actuating mechanism (not illustrated) is provided with a not-illustrated connection member, such as a link member. Via the connection member, such as a link member, the proximal end of the elevator wire 30 is connected to an elevating operation knob 16 provided to the operation portion 11.

Accordingly, as the surgeon operates the elevating operation knob 16 of the operation portion 11, the elevator wire 30 is operated and pulled via the above-described connection member, such as a link member, which forms the elevator base actuating mechanism. Thus, the treatment instrument elevator base 23 is operated and elevated about an elevator base rotation fulcrum 28. Thereby, a guide catheter and a guide wire 33, which are inserted into the treatment instrument insertion channel 26 and drawn out from the channel opening 15A, are elevated as the treatment instrument elevator base 23 is elevated.

A configuration of the distal end 15 of the insertion portion 10 will now be described with reference to FIG. 2.

As illustrated in FIG. 2, the distal end 15 is configured to include, for example, the rigid distal end portion 24 formed of metal, such as stainless steel, and forming the distal end body, and a distal end cover 25 formed of a nonconductive material, such as a resin, and covering a periphery of the rigid distal end portion 24.

The distal end cover 25 is fixed to the rigid distal end portion 24 by adhesion or the like. The distal end cover 25 is attached to the rigid distal end portion 24 to insulate the rigid distal end portion 24 and to ensure the airtight state, for example. The distal end cover 25 may be a disposable cover configured to be attachable and detachable with respect to the rigid distal end portion 24.

Further, the rigid distal end portion 24 is formed with an introduction guide path 27 for guiding the introduction of a treatment instrument or the like toward the distal end. The introduction guide path 27 is formed to communicate with the treatment instrument insertion channel (an insertion hole) 26, which serves as a treatment instrument insertion guide path provided in the insertion portion 10 of the endoscope 1.

The distal end side of the introduction guide path 27 is provided with a storage space 22 which is an open space formed by the rigid distal end portion 24 and the distal end cover 25. An opening of the storage space 22 forms the channel opening 15A which forms a distal end opening of the treatment instrument insertion channel 26.

Inside the storage space 22, the treatment instrument elevator base 23 is provided for elevating the treatment instruments, such as the guide wire 33 and a guide catheter, which are introduced through the treatment instrument insertion channel 26, to a desired position. The treatment instrument elevator base 23 is rotatably and axially supported at an end thereof by the elevator base rotation fulcrum 28 provided to the rigid distal end portion 24.

The elevator base rotation fulcrum 28 is disposed below a distal end opening of the introduction guide path 27. The treatment instrument elevator base 23 is installed to be able to perform an elevating movement by rotating about the elevator base rotation fulcrum 28 in the storage space 22 from a standby position indicated by the solid line in FIG. 2 to a treatment instrument elevated position indicated by the virtual line in the figure.

Further, the treatment instrument elevator base 23 is fixed with the distal end of the elevator wire 30. The elevator wire 30 is led to the operation portion 11 through a guide pipe 31 and a guide tube 32, which are inserted through the insertion portion 10, and is connected to the not-illustrated elevator base actuating mechanism described above. Furthermore, the treatment instrument elevator base 23 is configured to be operated and elevated about the elevator base rotation fulcrum 28 in accordance with the pulling operation of the elevator wire 30.

The endoscope 1 of the present embodiment is improved to be able to position the treatment instrument, such as the guide wire 33, by fixing the treatment instrument to an appropriate position on the treatment instrument elevator base 23, even if the treatment instrument is applied with external force.

The above-described configuration will now be specifically described with reference to FIGS. 2 to 7.

Figure 4:
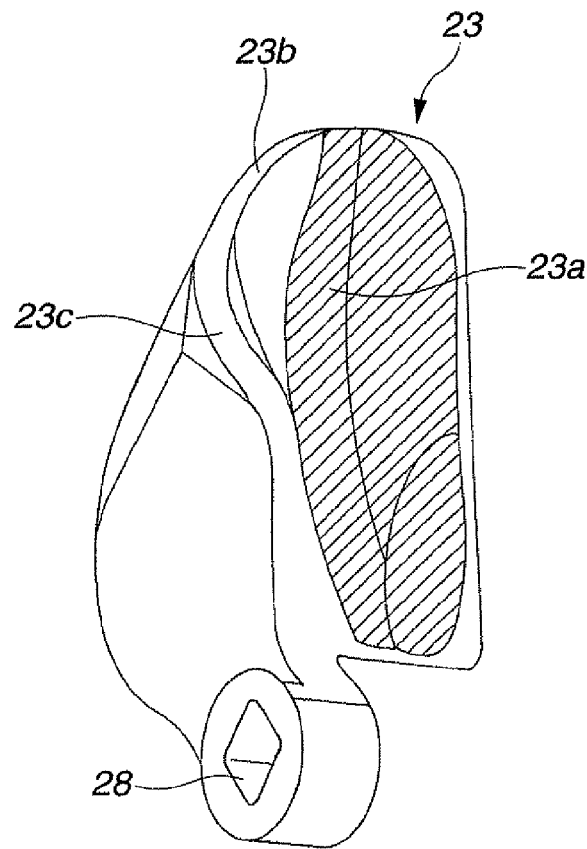
FIG. 4 is a perspective view according to the first embodiment of the present invention, illustrating a configuration of a treatment instrument elevator base provided in the distal end.
Figure 5:
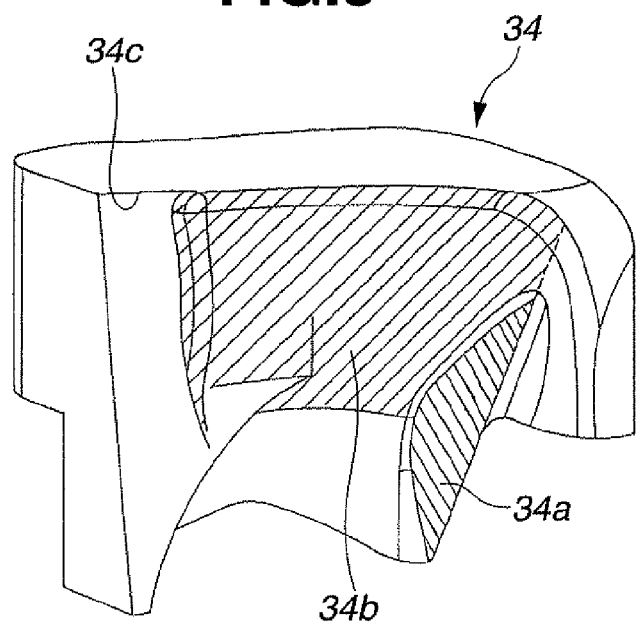
FIG. 5 is a perspective view according to the first embodiment of the present invention, illustrating a configuration of a contact portion provided in the distal end.
Figure 6:
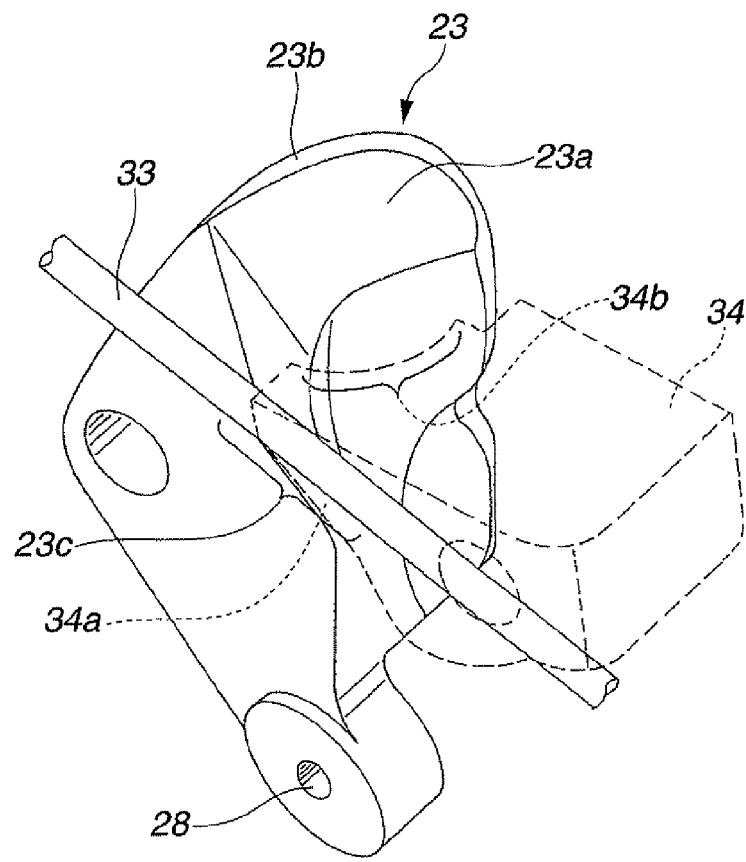
FIG. 6 is a perspective view according to the first embodiment of the present invention, illustrating a state in which a guide wire is fixed, being sandwiched by the treatment instrument elevator base in an elevating movement and the contact portion.
Figure 7:
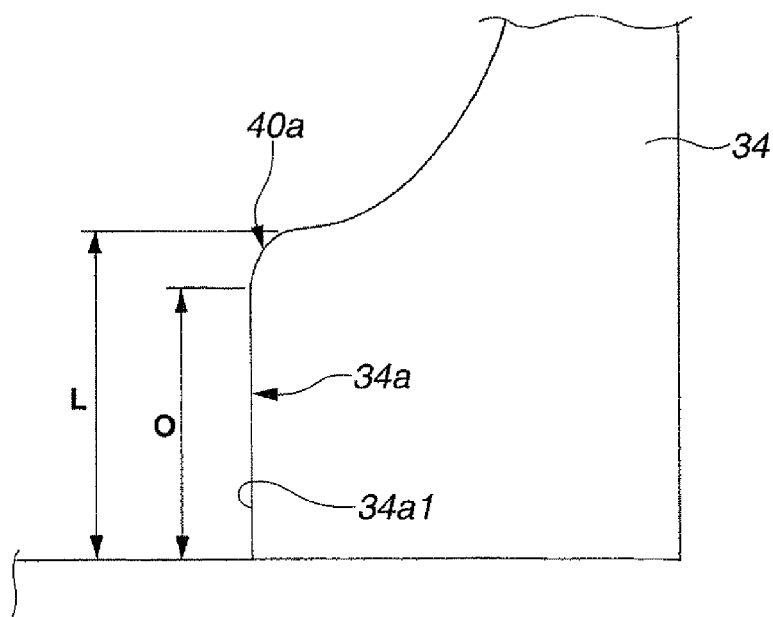
FIG. 7 is a plan view according to the first embodiment of the present invention, illustrating a specific configuration of a holding fixture portion of the contact portion illustrated in FIG. 5.

FIG. 4 is a perspective view illustrating a configuration of the treatment instrument elevator base provided in the distal end. FIG. 5 is a perspective view illustrating a configuration of a contact portion provided in the distal end. FIG. 6 is a perspective view illustrating a state in which the guide wire is fixed, being sandwiched by the treatment instrument elevator base in the elevating movement and the contact portion. FIG. 7 is a plan view illustrating a specific configuration of a holding fixture portion of the contact portion illustrated in FIG. 5.

As illustrated in FIGS. 2 and 3, the treatment instrument elevator base 23 is formed with a contact surface 23*a* which comes in contact with the treatment instrument, such as the guide wire 33 and the guide catheter. The contact surface 23*a* is formed by, for example, a tilted surface tilted with respect to the introduction axis of the introduction guide path 27.

An upper part of the contact surface 23*a* is formed with a first leading portion 23*b* for guiding and leading the treatment instrument, such as the guide wire 33, in accordance with the rotating movement (the elevating movement) of the treatment instrument elevator base 23, while being in contact with the treatment instrument.

The first leading portion 23*b* forms a part of the treatment instrument holding mechanism. Specifically, as illustrated in FIG. 4, the first leading portion 23*b* is formed such that an edge portion of the contact surface 23*a* of the treatment instrument elevator base 23 extending from the upper part of the contact surface 23*a* toward the objective lens 24*b*, for example, forms a tilted surface or a curved surface.

The degree of tilt of the first leading portion 23*b* or the degree of curvature (the degree R) of the curved surface is not particularly limited, as long as the degree of tilt or the degree of curvature allows the first leading portion 23*b* to smoothly lead the guide wire 33 in contact with the first leading portion 23*b* to a later-described holding portion 23*c* which forms the holding fixture portion of the treatment instrument elevator base 23.

Further, the first leading portion 23*b* of the treatment instrument elevator base 23 is provided with the holding portion 23*c* which is at least consecutive to the first leading portion 23*b* to sandwich and fix the guide wire 33. The holding portion 23*c* is formed as a part of the first leading portion 23*b*.

As illustrated in FIG. 4, the holding portion 23*c* is formed as a grasping surface having a predetermined size required to sandwich and hold the guide wire 33, which has a diameter not exceeding a predetermined value and is led by the first leading portion 23*b*, together with a later-described contact portion 34.

The guide wire 33 having a diameter not exceeding a predetermined value corresponds to the guide wire 33 used in a normal treatment and having a diameter in the range of from approximately 0.02 inches to approximately 0.04 inches, for example. However, the guide wire 33 is not limited to the guide wire 33 having the above-described diameter.

To increase the holding force for holding the guide wire 33, the grasping surface of the holding portion 23*c* may be formed into a circular arc shape to fit the circular arc shape of the guide wire 33 or into a substantially V-shaped groove, for example. Further, the grasping surface may be formed to have a large contact area with the guide wire 33. That is, the holding portion 23*c* is formed to have high holding force for holding the guide wire 33, irrespective of the shape of the grasping surface.

The rigid distal end portion 24, in which the treatment instrument elevator base 23 of the above configuration is rotatably attached, is provided with the contact portion 34 projecting toward the inside of the storage space 22 to form a part of the treatment instrument holding mechanism, as illustrated in FIGS. 2 and 3.

The contact portion 34 is formed by an insulating material, for example. As illustrated in FIGS. 3 and 5, a lower part of the contact portion 34 on the side of the objective lens 24*b*, for example, is formed with a holding fixture portion 34*a* which comes in contact with and fixes the guide wire 33 stored in the holding portion 23*c* of the treatment instrument elevator base 23.

The holding fixture portion 34*a* is formed to be located at a position opposite to the holding portion 23*c* of the treatment instrument elevator base 23 and to project toward the holding portion 23*c* when the treatment instrument elevator base 23 is elevated.

FIG. 7 illustrates a cross section in the horizontal direction of the holding fixture portion 34*a* of the contact portion 34. As illustrated in FIG. 7, the holding fixture portion 34*a* includes an effective holding portion 34*a*1 having a width required to reliably come in contact with and fix the above-described guide wire 33 having a diameter not exceeding a predetermined value (specifically, the small-diameter guide wire 33 having a diameter of approximately 0.02 inches, for example).

In the above case, it is desirable to set a width L of the holding fixture portion 34*a* to be less than a radius G (see FIG. 14) of a large-diameter treatment instrument 33A including the above-described treatment instrument such as a catheter. It is also desirable to set a width O of the effective holding portion 34*a*1 of the holding fixture portion 34*a* to be substantially the same as or at least equal to or greater than the diameter of the small-diameter guide wire 33.

Further, a corner portion 40*a* extending from the effective holding portion 34*a*1 to a later-described second leading portion 34*b* is formed into a circular arc shape, for example (see FIG. 7), to easily lead the large-diameter treatment instrument 33A including the treatment instrument such as a catheter, rather than the guide wire 33, to the later-described second leading portion 34*b*.

The shape of the corner portion 40*a* is not limited to the circular arc shape, and may be a tapered shape, for example. That is, the corner portion 40*a* can take any shape, as long as the shape allows the corner portion 40*a* to smoothly lead the large-diameter treatment instrument 33A including the treatment instrument such as a catheter to the second leading portion 34b.

The upper part of the contact portion 34 is formed with the second leading portion 34b for guiding and leading the large-diameter treatment instrument 33A including the treatment instrument such as a catheter, which is larger in size than the grasping surface of the holding portion 23c, in a direction away from the holding fixture portion 34a (a direction away from the objective lens 24b) in accordance with the rotating movement (the elevating movement) of the treatment instrument elevator base 23.

The large-diameter treatment instrument 33A including the treatment instrument such as a catheter, which is larger in size than the grasping surface of the holding portion 23c, is the treatment instrument having a diameter equal to or greater than approximately 0.04 inches, for example.

The second leading portion 34b forms a part of the treatment instrument holding mechanism. Specifically, as illustrated in FIGS. 5 and 7, the second leading portion 34b is formed such that an edge portion extending from the corner portion 40a of the holding fixture portion 34a in a direction opposite to the objective lens 24b forms a tilted surface or a curved surface.

The degree of tilt of the second leading portion 34b or the degree of curvature (the degree R) of the curved surface is not particularly limited, as long as the degree of tilt or the degree of curvature allows the second leading portion 34b to smoothly lead the large-diameter treatment instrument 33A including the treatment instrument such as a catheter, which is in contact with the second leading portion 34b, to a later-described holding fixture portion 34d.

Further, a portion of the second leading portion 34b apart from the holding fixture portion 34a by a predetermined distance is formed with the holding fixture portion 34d which holds and fixes the large-diameter treatment instrument 33A including the treatment instrument such as a catheter by sandwiching the large-diameter treatment instrument 33A together with the contact surface 23a of the treatment instrument elevator base 23. The holding fixture portion 34d is provided at a position opposite to the holding fixture portion 34a with respect to the second leading portion 34b.

Similarly to the holding portion 23c of the treatment instrument elevator base 23, the grasping surface of the holding fixture portion 34d may be formed into a circular arc shape to fit the circular arc shape of the large-diameter treatment instrument 33A including the treatment instrument such as a catheter or into a substantially V-shaped groove, for example. Further, the grasping surface may be formed to have a large contact area with the large-diameter treatment instrument 33A including the treatment instrument such as a catheter.

The present embodiment described above is configured such that the holding fixture portion 34d is provided on the second leading portion 34b of the contact portion 34. However, the configuration is not limited to the above. Thus, the embodiment may be configured such that the holding fixture portion 34d is not provided, and that a part of the second leading portion 34b and the contact surface 23a of the treatment instrument elevator base 23 hold and fix the large-diameter treatment instrument 33A including the treatment instrument such as a catheter.

The proximal end of the second leading portion 34b of the contact portion 34 is formed with a release groove 34c, in which an edge portion of the contact surface 23a of the treatment instrument elevator base 23 is inserted and released in the direction of the contact portion 34. Accordingly, the treatment instrument elevator base 23 and the contact portion 34 can sandwich the guide wire 33 or the large-diameter treatment instrument 33A including the treatment instrument such as a catheter, while obtaining predetermined holding force, and thus can hold and fix the guide wire 33 or the large-diameter treatment instrument 33A.

FIG. 6 illustrates the state in which the treatment instrument elevator base 23 forming the treatment instrument holding mechanism and the contact portion 34 provided to the rigid distal end portion 24 hold and fix the small-diameter guide wire 33 while sandwiching the guide wire 33. That is, the guide wire 33 is positioned and firmly grasped and fixed by the grasping surface formed by the holding portion 23c of the treatment instrument elevator base 23 and the holding fixture portion 34a of the contact portion 34.

Further, when the large-diameter treatment instrument 33A including the treatment instrument such as a catheter is employed, the large-diameter treatment instrument 33A including the treatment instrument such as a catheter is guided by the second leading portion 34b via the holding fixture portion 34a of the contact portion 34, and thereafter is positioned by the holding fixture portion 34d provided on the second leading portion 34b and by the contact surface 23a of the treatment instrument elevator base 23.

The operation of the endoscope 1 of the present embodiment will now be described with reference to FIGS. 8 to 14.

Figure 8:
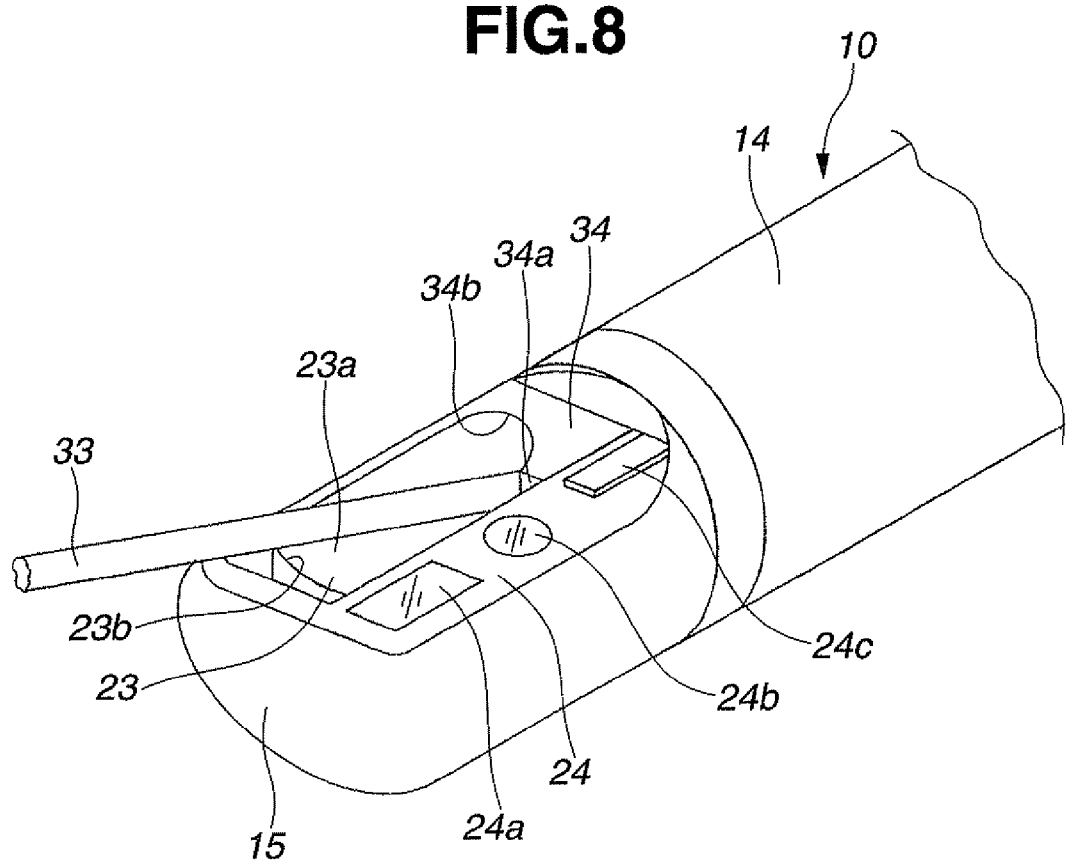
FIG. 8 is a perspective view for explaining the operation of the first embodiment, illustrating the exterior of the distal end in a state prior to the elevating movement of the treatment instrument elevator base, in which the guide wire is inserted in a distal end body.
Figure 9:
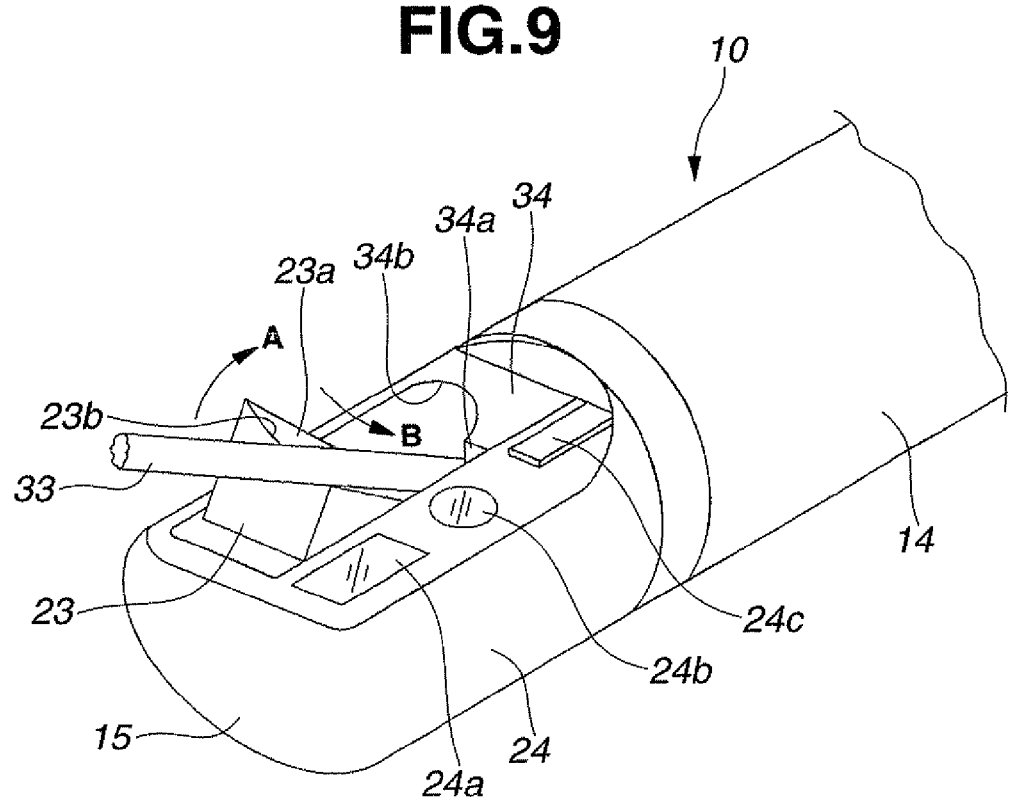
FIG. 9 is a perspective view for explaining the operation of the first embodiment, illustrating the exterior of the distal end in a state in which the treatment instrument elevator base is elevated from the state illustrated in FIG. 8 and the guide wire is led toward a fixing position by a first leading portion of the treatment instrument elevator base.
Figure 10:
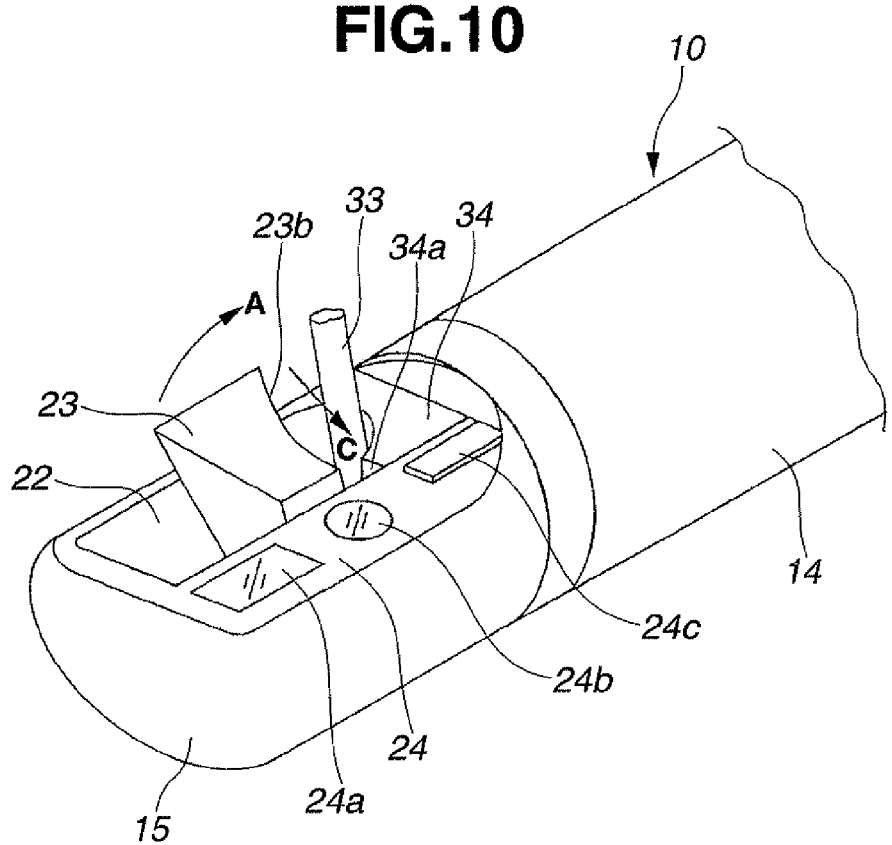
FIG. 10 is a perspective view for explaining the operation of the first embodiment, illustrating the exterior of the distal end in a state in which the guide wire is further moved from the state illustrated in FIG. 9 to the fixing position through the elevating movement of the treatment instrument elevator base and is fixed to the position.
Figure 11:
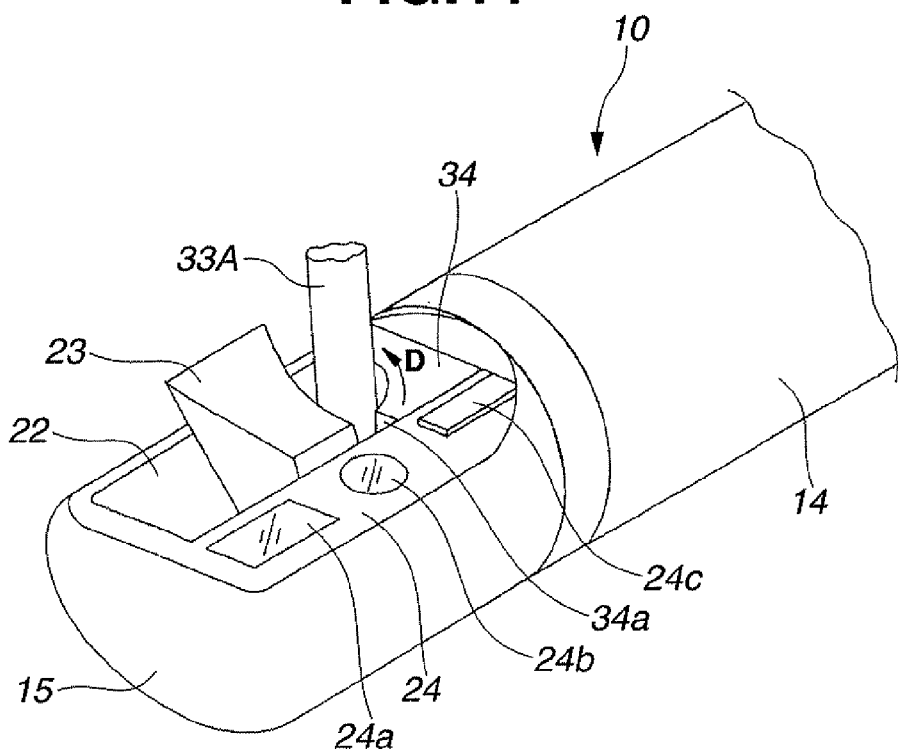
FIG. 11 is a perspective view according to the first embodiment of the present invention, illustrating the exterior of the distal end in a state in which a large-diameter treatment instrument including a treatment instrument such as a catheter is led and fixed to a maximum elevated position by a second leading portion of the contact portion through the elevating movement of the treatment instrument elevator base.
Figure 12:
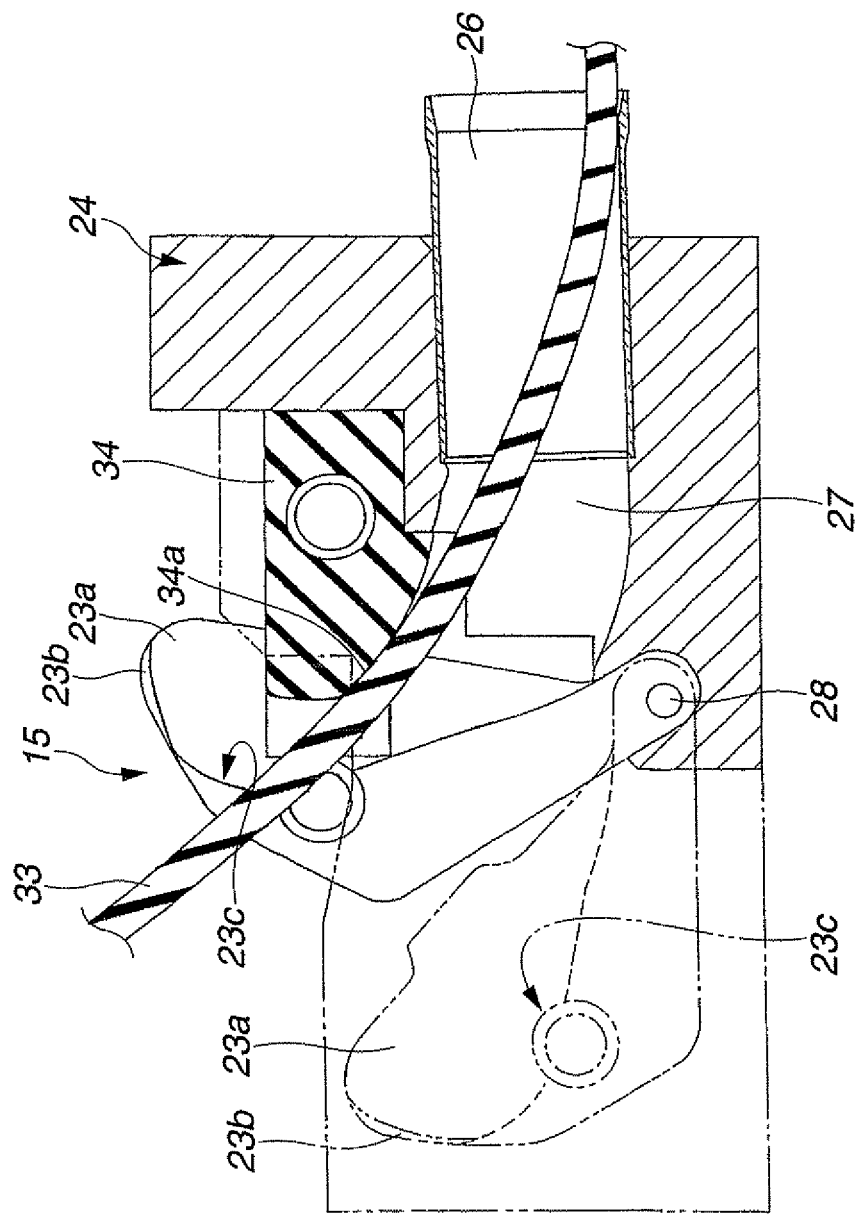
FIG. 12 is a cross-sectional view according to the first embodiment of the present invention in the direction of the insertion axis of the distal end illustrated in FIG. 10, illustrating a state in which the guide wire is grasped, being sandwiched by a holding portion of the treatment instrument elevator base and an end portion of the holding fixture portion of the contact portion.
Figure 13:
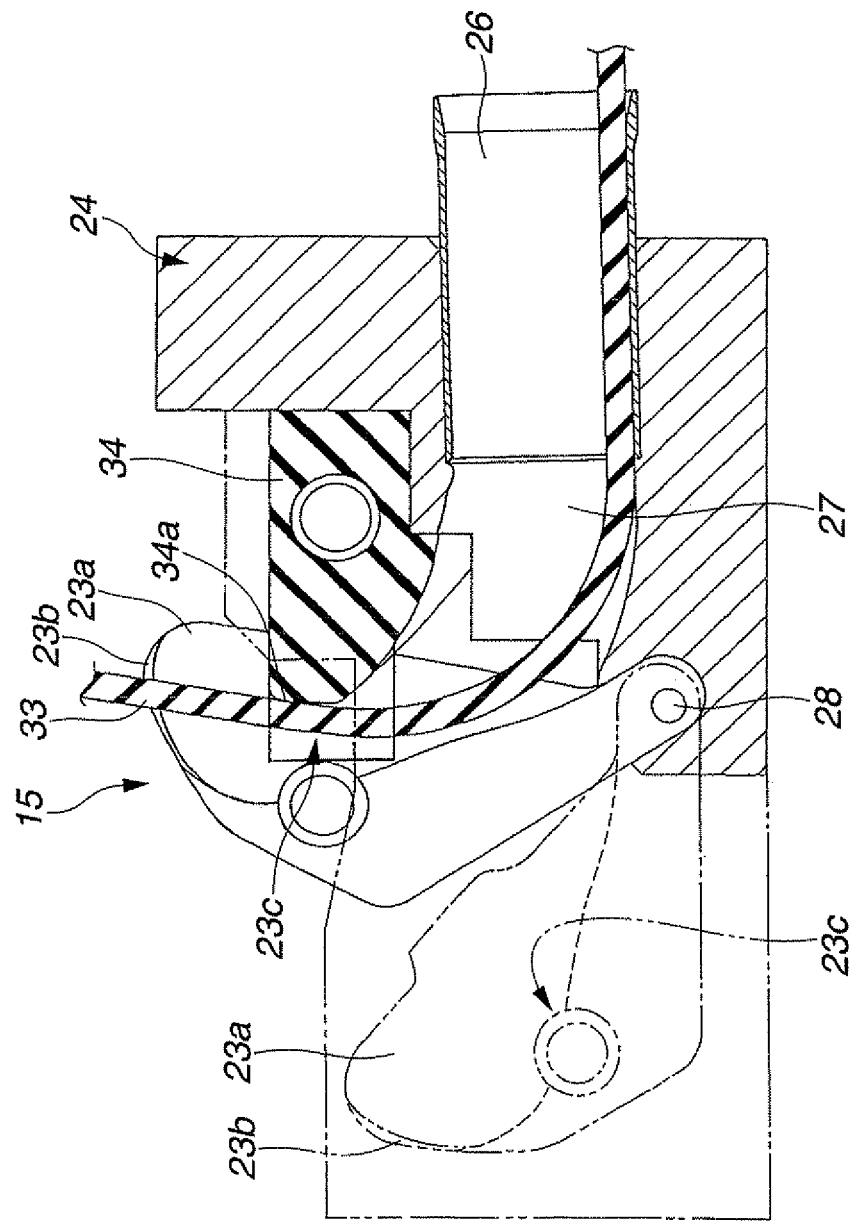
FIG. 13 is a cross-sectional view according to the first embodiment of the present invention in the direction of the insertion axis of the distal end illustrated in FIG. 10, illustrating a state in which the guide wire is grasped, being sandwiched by the holding portion of the treatment instrument elevator base and a surface of the holding fixture portion of the contact portion.
Figure 14:
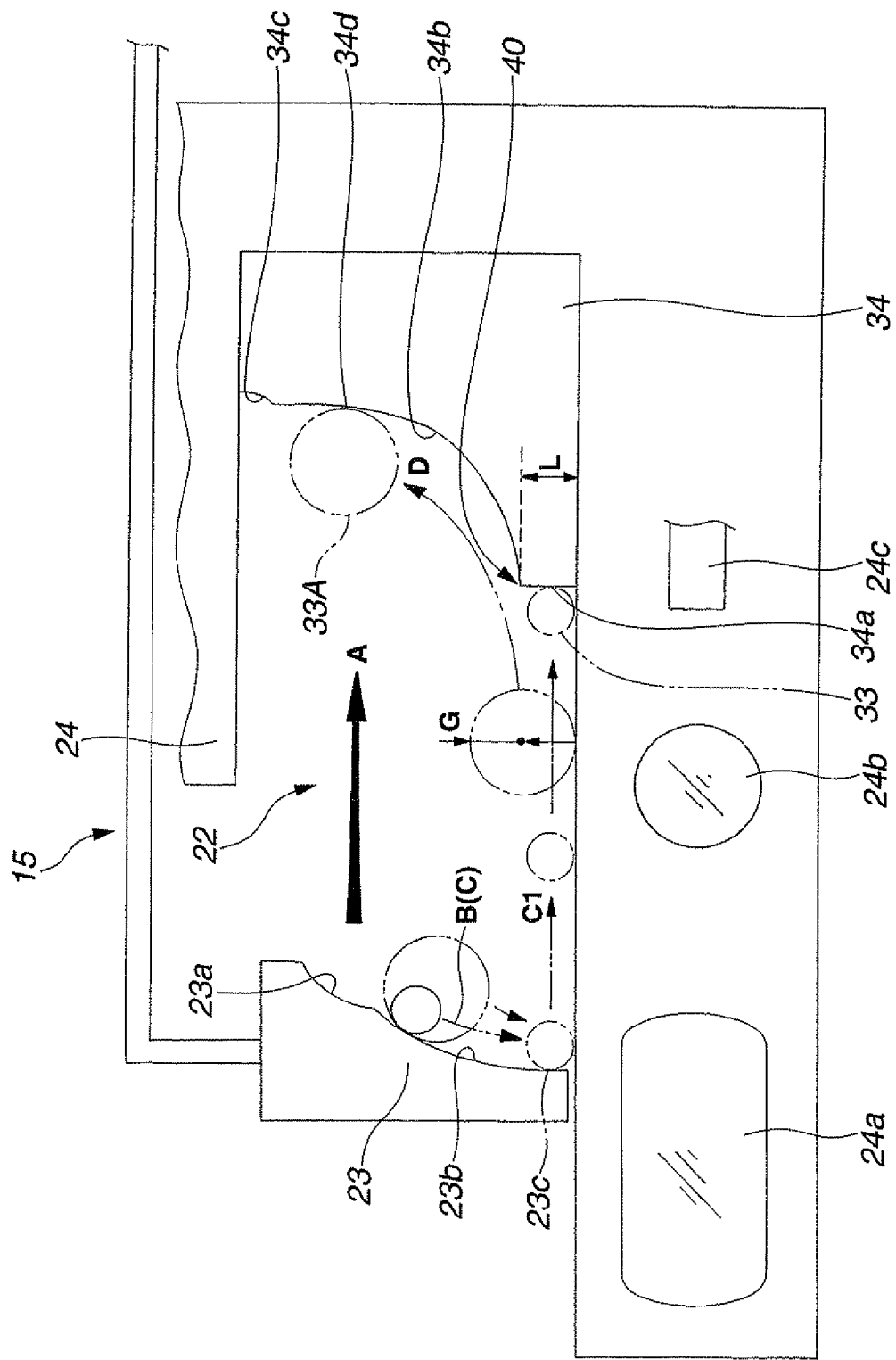
FIG. 14 is an operational view according to the first embodiment of the present invention for explaining the operation proceeding from the state illustrated in FIG. 8 to the state illustrated in FIG. 10 and to the state illustrated in FIG. 11.

FIGS. 8 to 14 are perspective views and cross-sectional views and the like for explaining the operation of the first embodiment, illustrating the exterior of the distal end in accordance with respective steps. FIG. 8 illustrates a state prior to the elevating movement of the treatment instrument elevator base, in which the guide wire is inserted in the distal end body. FIG. 9 illustrates a state in which the treatment instrument elevator base is elevated from the state illustrated in FIG. 8 and the guide wire is led toward a fixing position by the first leading portion of the treatment instrument elevator base. FIG. 10 illustrates a state in which the guide wire is further moved from the state illustrated in FIG. 9 to the fixing position through the elevating movement of the treatment instrument elevator base and is fixed to the position. FIG. 11 illustrates a state in which the large-diameter treatment instrument including the treatment instrument such as a catheter is led to a maximum elevated position by the second leading portion of the contact portion through the elevating movement of the treatment instrument elevator base. Further, FIG. 12 is a cross-sectional view in the direction of the insertion axis of the distal end illustrated in FIG. 10 in a state in which the guide wire is grasped, being sandwiched by the holding portion of the treatment instrument elevator base and the end portion of the holding fixture portion of the contact portion. FIG. 13 is a cross-sectional view in the direction of the insertion axis of the distal end illustrated in FIG. 10 in a state in which the guide wire is grasped, being sandwiched by the holding portion of the treatment instrument elevator base and a surface of the holding fixture portion of the contact portion. FIG. 14 is an operational view for explaining the operation proceeding from the state illustrated in FIG. 8 to the state illustrated in FIG. 10 and to the state illustrated in FIG. 11. The following description will be made on the assumption that the directions of the arrows A, B, C, and D shown in FIGS. 9 to 11 correspond to the directions of the arrows A, B, C, and D shown in FIG. 14.

It is now assumed that the surgeon performs observation or treatment of the pancreaticobiliary ducts by using the endoscope 1 of the first embodiment. In this case, the surgeon inserts a guide catheter into the treatment instrument insertion channel 26 from the insertion opening 21 of the operation portion 11 of the endoscope 1.

Then, the surgeon causes the guide catheter to project outside the channel opening 15A, and transpapillarily inserts the guide catheter into a pancreatic duct or a bile duct (not illustrated). Thereafter, the surgeon exchanges the currently used guide catheter with a treatment instrument which is to be used next.

In the above step, the surgeon first inserts the guide wire 33 from a cap provided on the proximal end side of the guide catheter. Then, the surgeon confirms under X-ray illumination that the distal end of the guide wire 33 has been inserted inside the pancreatic duct or the bile duct, and thereafter grasps by hand the proximal end side of the guide wire 33.

In the above state, the surgeon subsequently performs an operation of withdrawing the guide catheter. The surgeon confirms from an observed image that the guide catheter has been withdrawn from the papilla, and thereafter withdraws the guide catheter further toward the proximal side.

Then, in the state in which the distal end of the guide catheter is stored in the channel opening 15A, the surgeon operates the elevating operation knob 16 of the operation portion 11. FIG. 8 illustrates the state prior to the operation of the elevating operation knob 16 and thus prior to the elevation of the treatment instrument elevator base 23. That is, as illustrated in FIG. 8, the guide wire 33 projecting from the channel opening 15A is made in contact with the contact surface 23a of the treatment instrument elevator base 23 or a part of the treatment instrument elevator base 23 by the reaction force of the guide wire 33 itself.

In the above state, the elevator wire 30 is operated and pulled in accordance with the operation of the elevating operation knob 16, and the treatment instrument elevator base 23 is rotated about the elevator base rotation fulcrum 28 to be elevated as indicated by the virtual line in FIG. 2 (or the solid line in FIG. 6).

FIG. 8 illustrates the state of the guide wire 33 brought about in accordance with the initial elevating movement of the treatment instrument elevator base 23. That is, as illustrated in FIG. 8, when the elevating movement of the treatment instrument elevator base 23 (the elevating movement in the direction of the arrow A shown in FIG. 9) starts from the state illustrated in FIG. 8, the guide wire 33 is guided and led to the holding portion 23c of the treatment instrument elevator base 23, while being in contact with the first leading portion 23b via the contact surface 23a of the treatment instrument elevator base 23, with which the guide wire 33 is in contact.

The operation of the above process will be described more in detail. As illustrated in FIG. 14, when the elevating movement of the treatment instrument elevator base 23 starts in the direction of the arrow A shown in FIG. 14, the guide wire 33 is led in the direction of the arrow B shown in FIG. 14, while being in contact with the first leading a portion 23b. That is, the guide wire 33 is led to the holding portion 23c of the treatment instrument elevator base 23 by the first leading portion 23b.

Similarly, when the large-diameter treatment instrument 33A including the treatment instrument such as a catheter is employed, the large-diameter treatment instrument 33A including the treatment instrument such as a catheter is led to the holding portion 23c of the treatment instrument elevator base 23, as illustrated in FIG. 14, via the contact surface 23a and the first leading portion 23b, with which the large-diameter treatment instrument 33A is made in contact by the reaction force thereof.

Further, due to the elevation of the treatment instrument elevator base 23 in the direction of the arrow A shown in FIG. 9, the guide wire 33 is led to the proximal end of the first leading portion 23b of the treatment instrument elevator base 23 (in the direction of the arrow C shown in FIG. 10) and made in contact with the holding portion 23c of the treatment instrument elevator base 23, as illustrated in FIGS. 10 and 14. When the treatment instrument elevator base 23 is further elevated, the guide wire 33 is moved in the direction of the arrow C shown in FIG. 14, while being kept in contact with the holding portion 23e. Thereafter, the guide wire 33 is made in contact with and pressed against the holding fixture portion 34a provided to the contact portion 34 of the rigid distal end portion 24 (see FIG. 14).

In the above process, the rigid guide wire 33 exerts the reaction force to keep the linear shape thereof. Accordingly, the guide wire 33 is pressed into the holding portion 23c by the reaction force to be firmly locked therein. At the same time, in the above state, the guide wire 33 is mechanically and firmly fixed, being sandwiched by the holding portion 23c and the holding fixture portion 34a of the contact portion 34, and being positioned to the holding portion 23c, i.e., the predetermined fixing position, through the contact of the holding fixture portion 34a with the guide wire 33, as illustrated in FIGS. 10, 12, and 14. FIGS. 10, 12, and 13 illustrate the state in which the guide wire 33 is firmly fixed to the predetermined position of the holding portion 23c of the treatment instrument elevator base 23 by the holding fixture portion 34a of the contact portion 34.

That is, in accordance with the elevation of the treatment instrument elevator base 23, the guide wire 33 is grasped and fixed by an end portion of the holding fixture portion 34a and the holding portion 23c, as illustrated in FIG. 12. Then, the guide wire 33 is grasped and fixed by the surface of the holding fixture portion 34a and the holding portion 23c, as illustrated in FIG. 13. The fixed state can be adjusted according to the amount of operation of the not-illustrated operation portion. The fixed state can be also adjusted according to the difference in the degree of rigidity of the guide wire 33 itself.

Meanwhile, when the large-diameter treatment instrument 33A including the treatment instrument such as a catheter is employed, the large-diameter treatment instrument 33A including the treatment instrument such as a catheter is led by the first leading portion 23b of the treatment instrument elevator base 23 to the proximal end of the first leading portion 23b (in the direction of the arrow C shown in FIG. 14), as in the case of the guide wire 33. However, a subsequent operation is different from the operation of the guide wire 33.

That is, the large-diameter treatment instrument 33A including the treatment instrument such as a catheter is larger in size than the grasping surface of the holding portion 23c (e.g., the width L, see FIGS. 7 and 14). Thus, due to the force applied in accordance with the rotating movement (the elevating movement) of the treatment instrument elevator base 23, the large-diameter treatment instrument 33A is lead to the second leading portion 34b of the contact portion 34 (in the direction of the arrow D shown in FIGS. 11 and 14) via the effective holding portion 34a1 (see FIG. 7) of the holding fixture portion 34a and the corner portion 40a. That is, the large-diameter treatment instrument 33A including the treatment instrument such as a catheter is not locked by the holding fixture portion 34a of the contact portion 34.

Thereafter, in accordance with the elevation of the treatment instrument elevator base 23, the large-diameter treatment instrument 33A including the treatment instrument such as a catheter is guided and led by the second leading portion 34b of the contact portion 34 in the direction away from the holding fixture portion 34a (the direction away from the objective lens 24b and indicated by the arrow D shown in FIGS. 11 and 14), while being pressed by the contact surface 23a.

Thereafter, as the treatment instrument elevator base 23 is further elevated, the large-diameter treatment instrument 33A including the treatment instrument such as a catheter is led to a part of the second leading portion 34b or the holding fixture portion 34d provided to the second leading portion 34b, and is made in contact with and pressed against the second leading portion 34b or the holding fixture portion 34d provided to the second leading portion 34b (see FIG. 14).

Then, the surgeon confirms that the guide wire 33 has been fixed, and thereafter completely withdraws the guide catheter to the outside of the treatment instrument insertion channel 26 from the side of the operation portion 11 of the endoscope 1. Thereafter, the surgeon inserts the treatment instrument which is to be used next from the proximal end side of the guide wire 33.

In the above step, the surgeon inserts the treatment instrument into the treatment instrument insertion channel 26, while using the guide wire 33 as a guide. Then, when the distal end of the treatment instrument comes in contact with the treatment instrument elevator base 23, the surgeon operates the elevating operation knob 16 to lay down the treatment instrument elevator base 23. Accordingly, when the treatment instrument passes the treatment instrument elevator base 23, the guide wire 33 is pushed out of the holding portion 23c by the pressing force of the treatment instrument and is released from the fixed state. Then, the surgeon further inserts the treatment instrument into the pancreatic duct or the bile duct.

According to the first embodiment, therefore, the guide wire 33, which is a treatment instrument, is mechanically fixed, being sandwiched by the holding portion 23c of the treatment instrument elevator base 23 and the holding fixture portion 34a of the contact portion 34. Therefore, the endoscope 1 of the present embodiment can firmly fix and hold the guide wire 33 to an appropriate position in the holding portion 23c of the treatment instrument elevator base 23, even if the guide wire 33 is applied with external force due to the movement of the insertion portion 10, for example.

Further, the endoscope 1 of the present embodiment includes the first leading portion 23b of the treatment instrument elevator base 23 and the second leading portion 34b of the contact portion 34. Thus, when the large-diameter treatment instrument 33A including the treatment instrument such as a catheter is employed, the large-diameter treatment instrument 33A including the treatment instrument such as a catheter can be smoothly led to the predetermined maximum elevated position by the second leading portion 34b simply by elevating the treatment instrument elevator base 23. Accordingly, the endoscope 1 of the present embodiment can prevent the treatment instrument from being kinked.

Furthermore, in the endoscope 1 of the present embodiment, the grasping surface formed by the holding portion 23c of the treatment instrument elevator base 23 and the holding fixture portion 34a of the contact portion 34 is formed into a circular shape or a groove shape. Therefore, the endoscope 1 of the present embodiment can stably and firmly lock the guide wire 33 in the holding portion 23c, even if the outer diameter of the guide wire 33 is slightly changed.

In the first embodiment, the first leading portion 23b and the holding portion 23c of the treatment instrument elevator base 23 and the holding fixture portion 34a and the second leading portion 34b of the contact portion 34 are disposed such that the guide wire 33 is fixed to the side in the vicinity of the objective lens 24b. However, the disposition is not limited to the above.

That is, according to the disposition of the present embodiment, the fixed state of the guide wire 33 fixed and held in the distal end 15, for example, can be reliably confirmed from an endoscopic image. Conversely to the first embodiment, if the first leading portion 23b and the holding portion 23c of the treatment instrument elevator base 23 and the holding fixture portion 34a and the second leading portion 34b of the contact portion 34 are disposed such that the guide wire 33 is fixed to the side opposite to the objective lens 24b, the range of visual field covering the fixed guide wire 33 can be expanded. Therefore, the endoscope 1 of the present embodiment can have the effect of improving the operability.

Second Embodiment

A second embodiment of the endoscope of the present invention will now be described with reference to FIG. 15.

Figure 15:
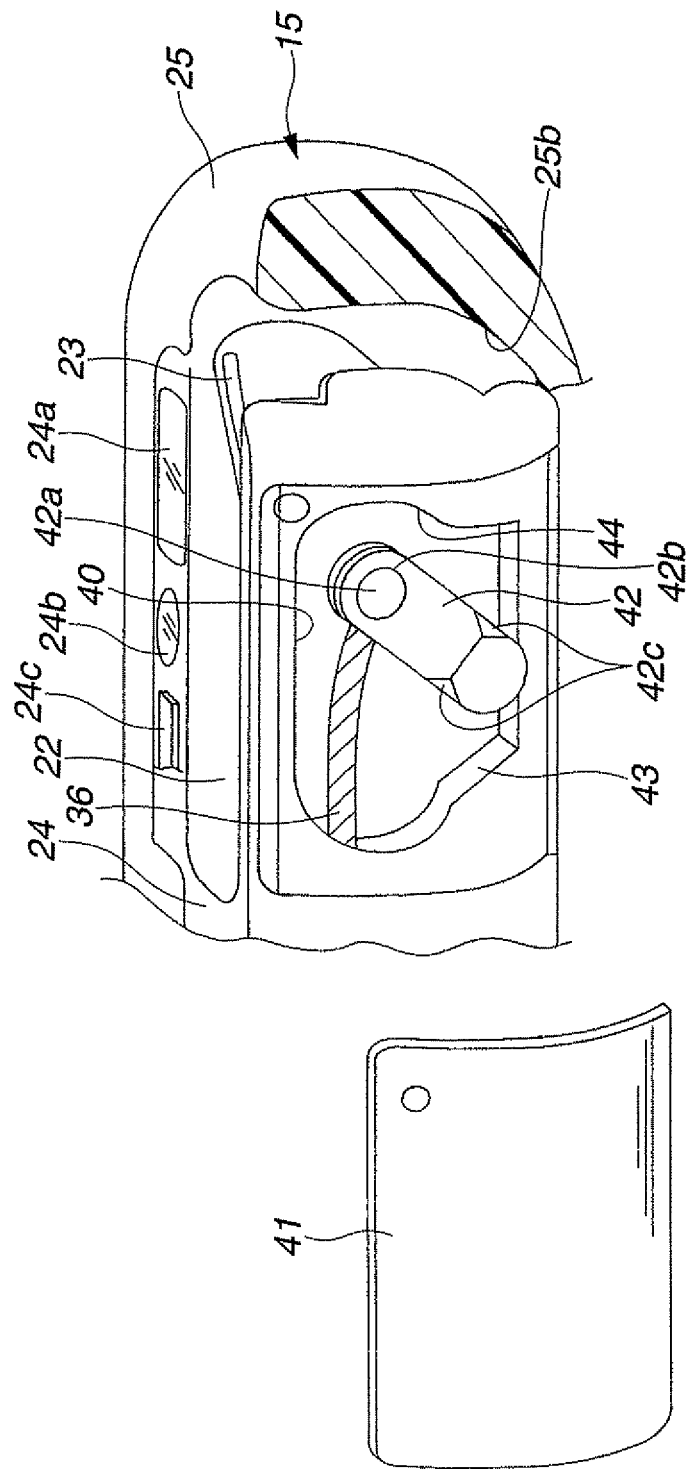
FIG. 15 is a partially exploded perspective view according to a second embodiment of the endoscope of the present invention, illustrating a state in which a drive arm of the distal end of the endoscope is rotated.

FIG. 15 relates to the second embodiment of the endoscope of the present invention, and is a partially exploded perspective view illustrating a state in which a drive arm of the distal end of the endoscope is rotated. The components of FIG. 15 similar to the components of the first embodiment will be denoted by the same reference numerals, and the description thereof will be omitted. Description will be made only of components different from the components of the first embodiment.

As illustrated in FIG. 15, the rigid distal end portion 24 of the endoscope 1 of the second embodiment is provided with a drive arm 42 for operating and rotating the treatment instrument elevator base 23. The drive arm 42 is disposed in a concave portion 40, which is recessed from the outer circumference of the rigid distal end portion 24 to have a circular arc (circular arc in the direction of the axis line) cross-section, to be rotated by remote control. The surface of the concave portion 40 is covered by a cover member 41.

The cover member 41 is for sealing the opening of the concave portion 40 to prevent the drive arm 42 from failing to operate due to waste fluid in the body. Further, the cover member 41 is detachably attached to the rigid distal end portion 24 by means of adhesion with an adhesive agent of weak adhesive force or application of a sealing agent and fixation with screws, for example.

An operation wire 36 for rotating the drive arm 42 is operated and moved back and forth by the elevating operation knob 16 of the operation portion 11. The operation wire 36 includes a wire connection member 42a fixed to the distal end thereof and rotatably attached in a wire communication hole 42b formed in the vicinity of the distal end of the drive arm 42.

Although not illustrated, the proximal end side of the drive arm 42 is integrally formed with a connecting shaft portion extending perpendicularly to the drive arm 42. The connecting shaft portion is axially and rotatably supported by the rigid distal end portion 24. Further, an angular shaft portion formed to the distal end of the connecting shaft portion is fit in a shaft hole of the treatment instrument elevator base 23.

According to the above configuration, by connecting the drive arm 42 via the connecting shaft portion (not illustrated) when the operation wire 36 is operated and moved back and forth, the treatment instrument elevator base 23 rotated about the rotation axis (the elevator base rotation fulcrum) 28 (see FIG. 2) together with the drive arm 42.

The drive arm 42 is provided with a first chamfer 42c and a second chamfer 42c for preventing the contact between the drive arm 42 and the concave portion 40 due to the variation in processing tolerance of the drive arm 42 or the concave portion 40, for example.

In the present embodiment, the proximal side of the concave portion 40 of the rigid distal end portion 24 is provided with a first controlling portion 43 for controlling the rotation of the drive arm 42 in the direction of the operation portion 11, and the distal end side of the concave portion 40 is provided with a second controlling portion 44 for controlling the rotation of the drive arm 42 in the direction of insertion.

Each of the first controlling portion 43 and the second controlling portion 44 is formed by a portion of a certain thickness forming the concave portion 40 and having a contact surface projecting in the direction of the drive arm 42 by a predetermined length. That is, as the drive arm 42 is made in contact with the first controlling portion 43 and the second controlling portion 44, the rotated drive arm 42 can be controlled in terms of the range of rotation.

The present embodiment further includes a third controlling portion 25a or 25b which controls the rotating movement of the treatment instrument elevator base 23, as the means for preventing a reduction in resistance of the drive arm 42.

The third controlling portion 25a or 25b is provided at a predetermined position inside the distal end cover 25, as illustrated in FIG. 2 or 15, for example. That is, the third controlling portion 25a or 25b is formed to have a contact surface projecting inward by a predetermined length. In other words, as the treatment instrument elevator base 23 is made in contact with the third controlling portion 25a or 25b, the range of rotation of the treatment instrument elevator base 23 is controlled. As a result, the range of rotation of the drive arm 42 connected to the treatment instrument elevator base 23 can be also controlled.

Other configurations and operations of the present embodiment are similar to the configurations and operations of the first embodiment.

Therefore, according to the present embodiment, in addition to the effects of the first embodiment, the movable range of the drive arm 42 can be controlled. Accordingly, the present embodiment can provide the effect of improving the resistance of the drive arm 42.

The second embodiment described above is configured such that the first to third controlling portions 43, 44, and 25a (25b) are provided. However, similar effects to the effects of the above configuration can be obtained by providing at least one of the controlling portions, instead of providing all of the controlling portions. Further, the first to third controlling portions 43, 44, and 25a (25b) are not limited to the portions of a certain thickness forming the concave portion 40 and the projecting portion projecting from the bottom surface of the distal end cover 25, respectively. Thus, a pin may be used, for example, to control the movable range of the drive arm 42 or the treatment instrument elevator base 23.

Third Embodiment

A third embodiment of the endoscope of the present invention will now be described with reference to FIGS. 16 to 33.

Figure 16:
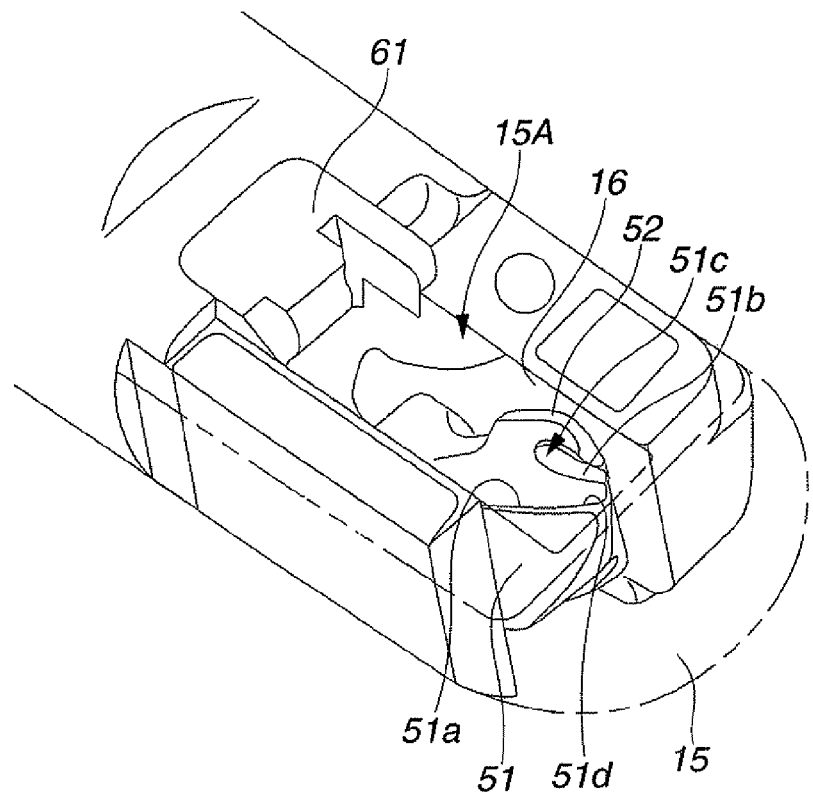
FIG. 16 is a perspective view according to a third embodiment of the endoscope of the present invention, illustrating an external configuration of the distal end of the endoscope in a laid state of a treatment instrument elevator base.
Figure 17:
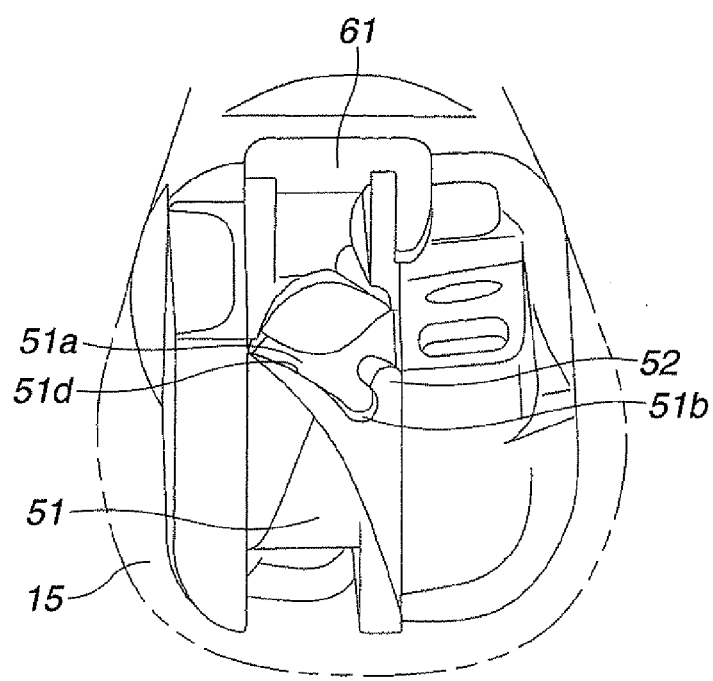
FIG. 17 is a perspective view according to the third embodiment of the endoscope of the present invention, illustrating the distal end of the endoscope illustrated in FIG. 16, as viewed from the front side.
Figure 18:
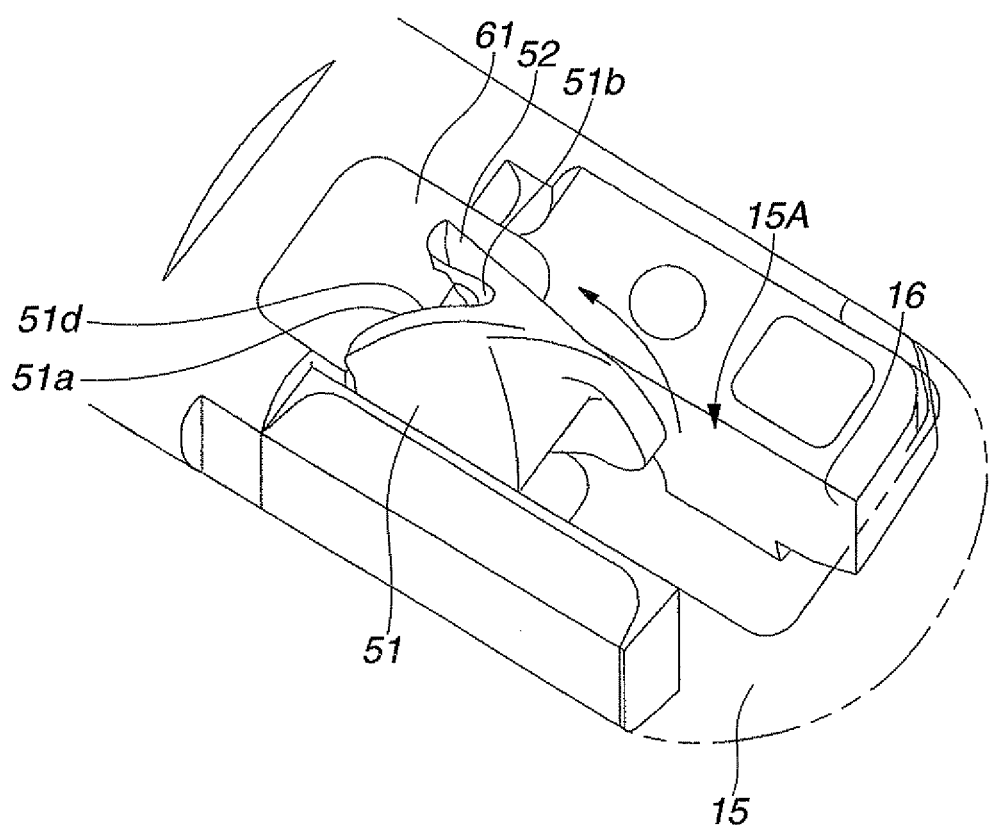
FIG. 18 is a perspective view according to the third embodiment of the endoscope of the present invention, illustrating the external configuration of the distal end in an elevated state of the treatment instrument elevator base.
Figure 19:
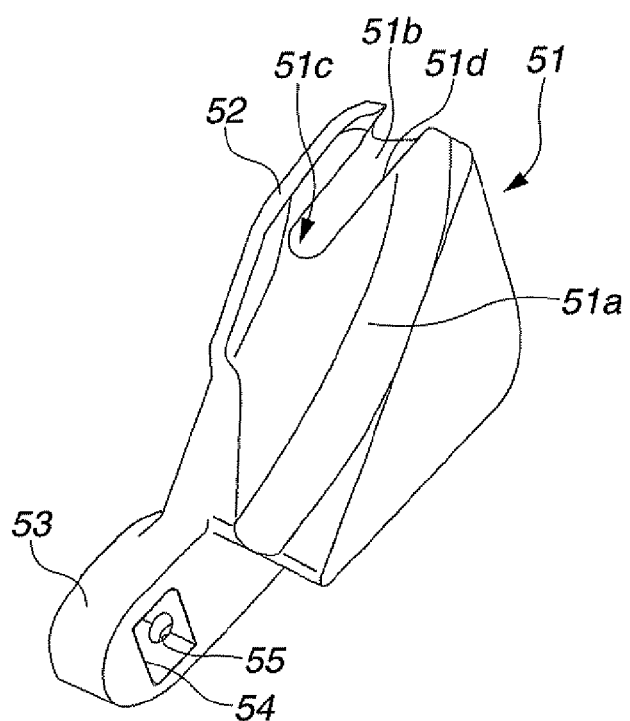
FIG. 19 is a perspective view according to the third embodiment of the endoscope of the present invention, illustrating the exterior of the treatment instrument elevator base.
Figure 20:
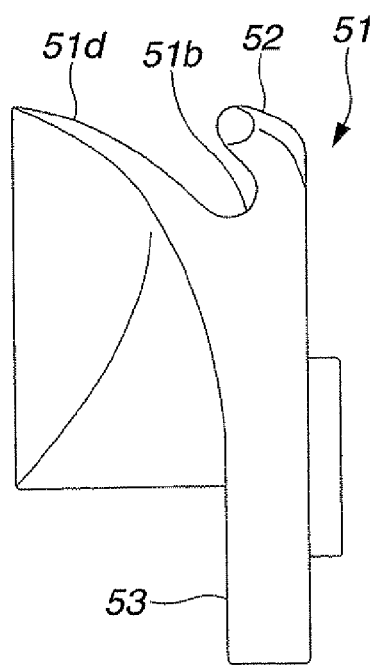
FIG. 20 is a front view according to the third embodiment of the endoscope of the present invention, illustrating the treatment instrument elevator base illustrated in FIG. 19.
Figure 21:
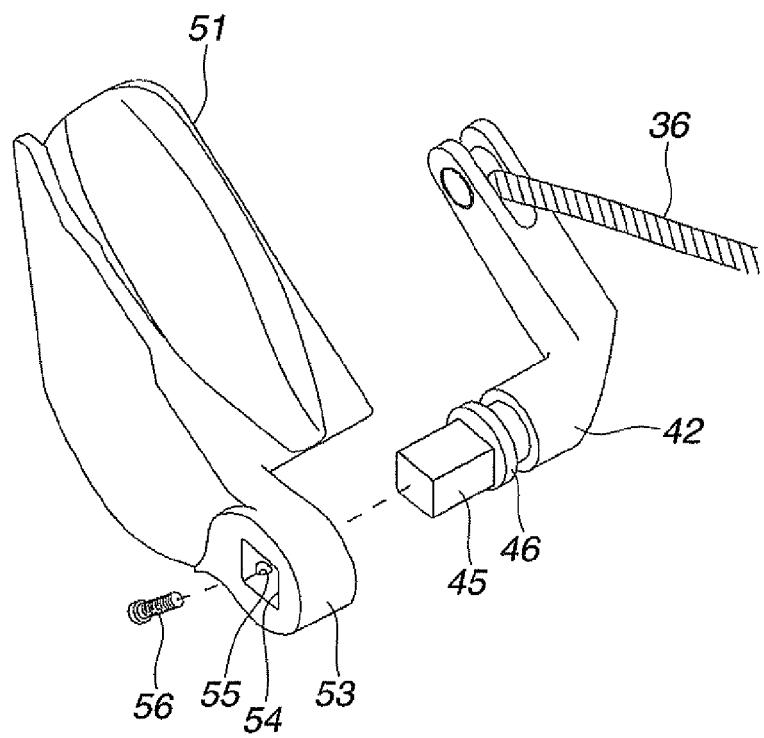
FIG. 21 is an exploded perspective view according to the third embodiment of the endoscope of the present invention, illustrating the treatment instrument elevator base and a drive arm to be attached to the treatment instrument elevator base.
Figure 22:
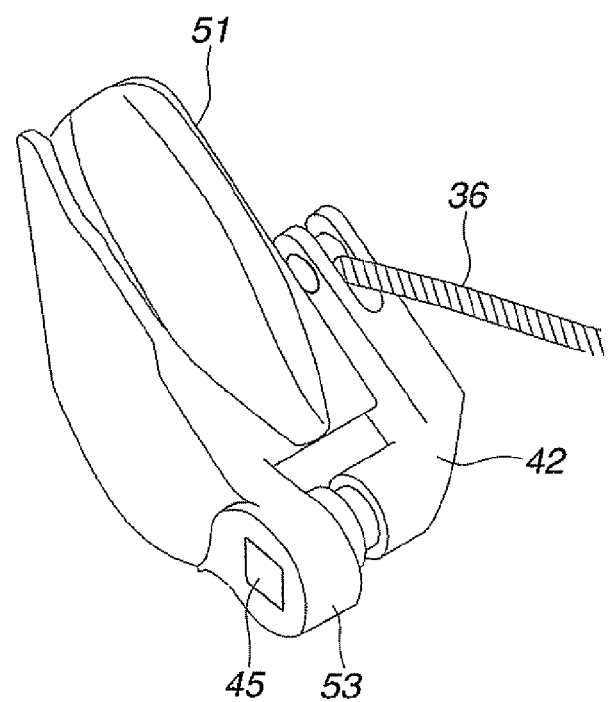
FIG. 22 is a perspective view according to the third embodiment of the endoscope of the present invention, illustrating the treatment instrument elevator base attached with the drive arm.
Figure 23:
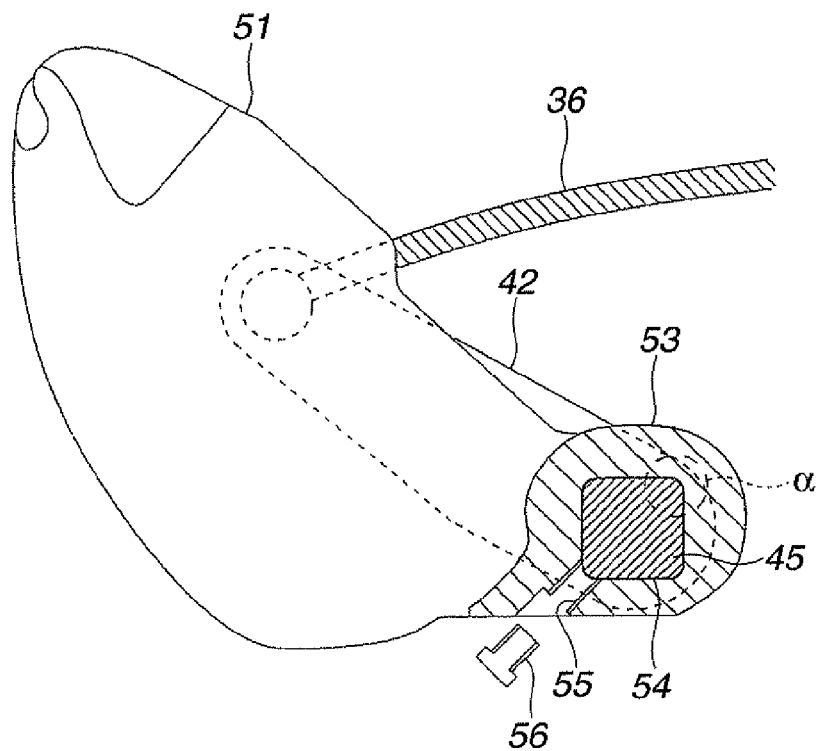
FIG. 23 is a partial cross-sectional view according to the third embodiment of the endoscope of the present invention, illustrating an attached state of a rotation shaft of the drive arm to the treatment instrument elevator base.
Figure 24:
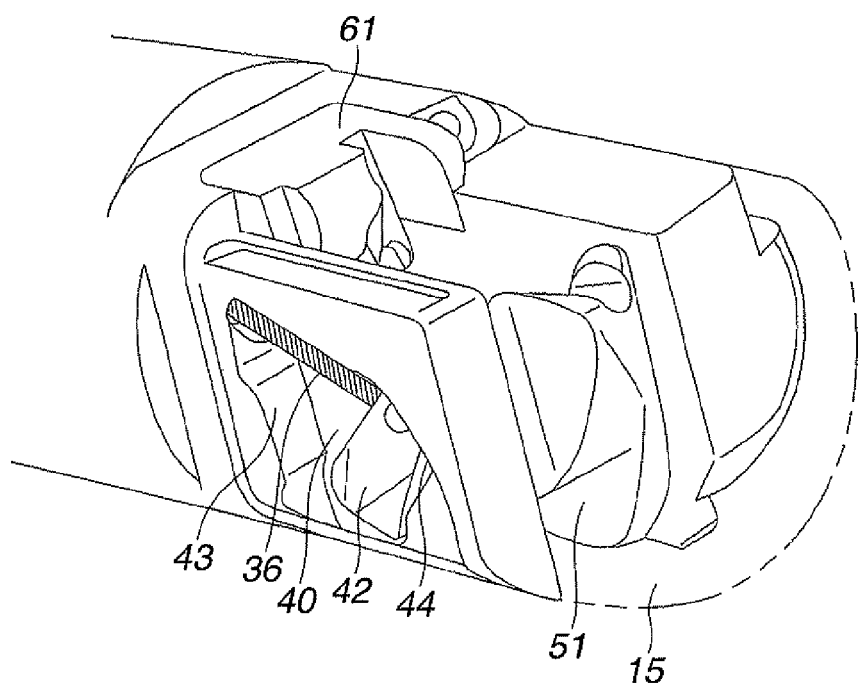
FIG. 24 is a perspective view according to the third embodiment of the endoscope of the present invention, illustrating the distal end of the endoscope in which the drive arm is shown.
Figure 25:
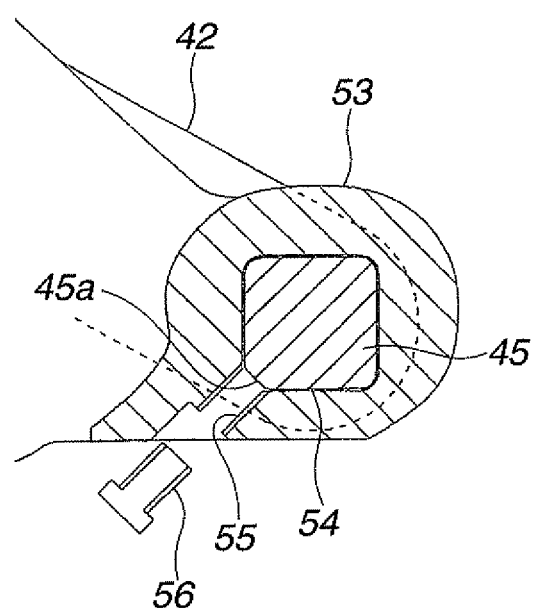
FIG. 25 is a partial cross-sectional view of a modified example according to the third embodiment of the endoscope of the present invention, illustrating an attached state of the rotation shaft of the drive arm to the treatment instrument elevator base.
Figure 26:
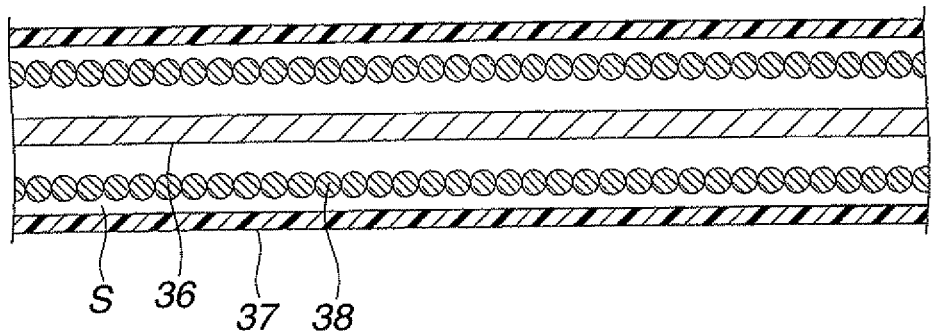
FIG. 26 is a cross-sectional view according to a conventional example, illustrating a protection tube and a coil tube, through which an operation wire is inserted.
Figure 27:
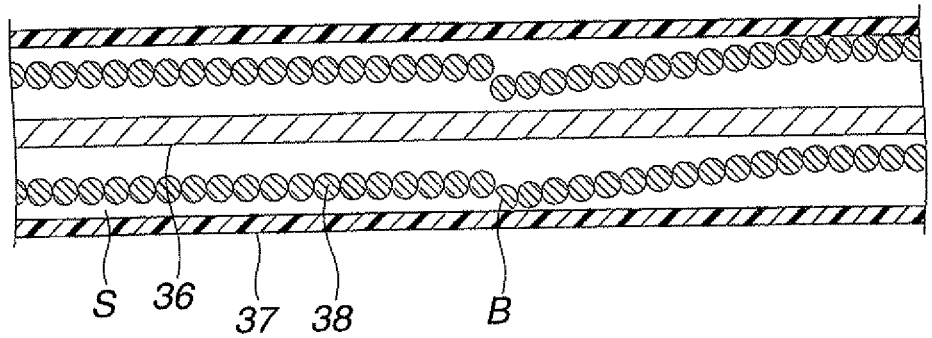
FIG. 27 is a cross-sectional view of the protection tube and the coil tube, through which the operation wire is inserted, in a state in which the coil tube illustrated in FIG. 26 is damaged.
Figure 28:
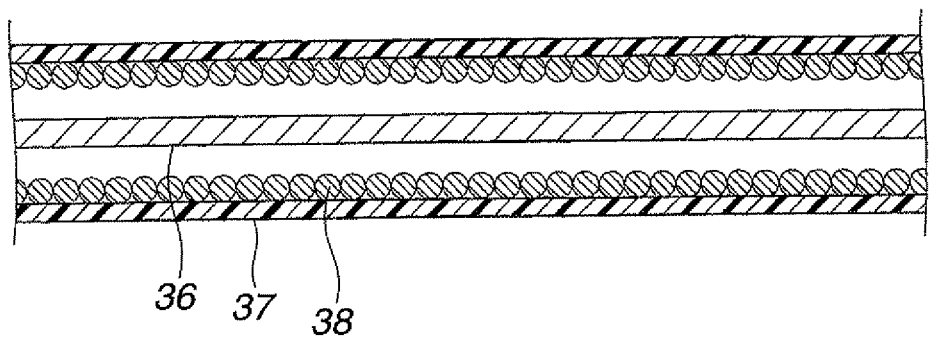
FIG. 28 is a cross-sectional view according to the third embodiment of the endoscope of the present invention, illustrating the protection tube and the coil tube, through which the operation wire is inserted.
Figure 29:
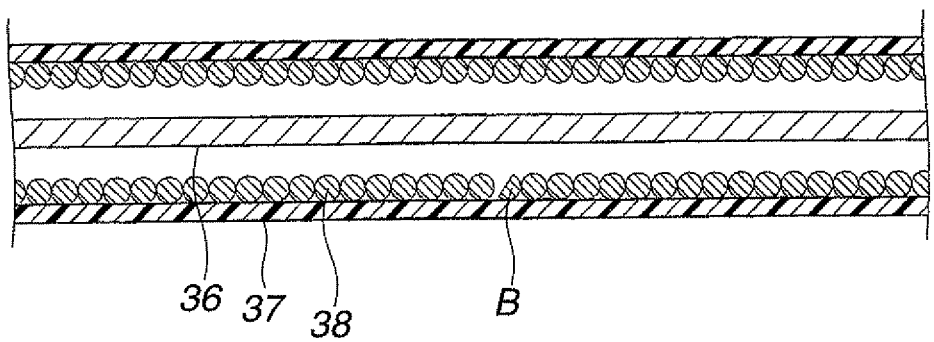
FIG. 29 is a cross-sectional view according to the third embodiment of the endoscope of the present invention, illustrating the protection tube and the coil tube, through which the operation wire is inserted, in a state in which the coil tube illustrated in FIG. 28 is damaged.
Figure 30:
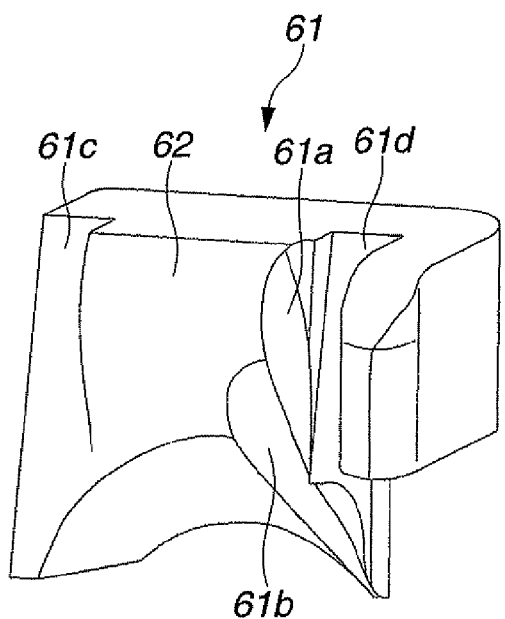
FIG. 30 is a perspective view according to the third embodiment of the endoscope of the present invention, illustrating an insulating block.
Figure 31:
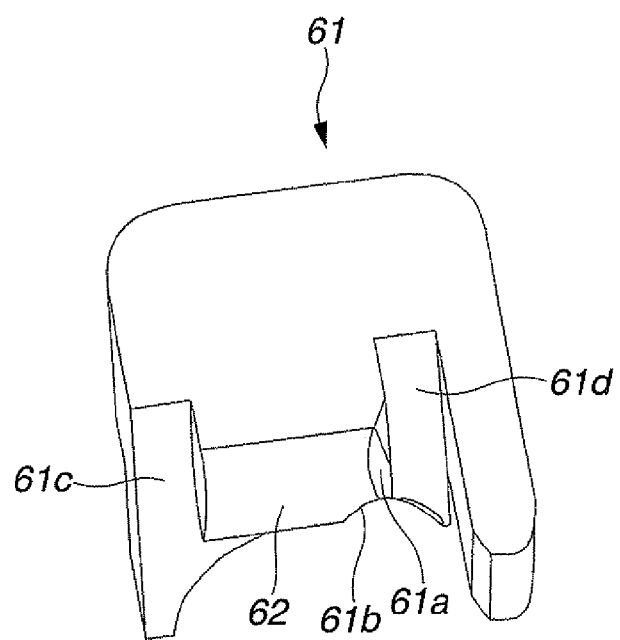
FIG. 31 is a perspective view according to the third embodiment of the endoscope of the present invention, illustrating the insulating block, as viewed in a different angle from the angle of FIG. 30.
Figure 32:
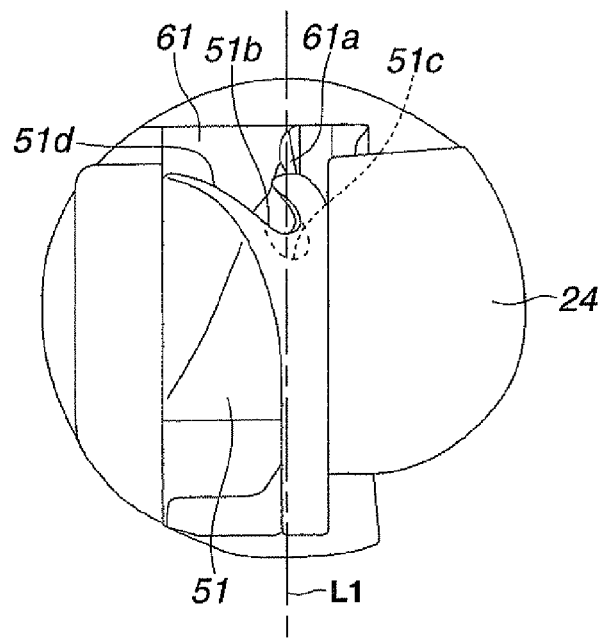
FIG. 32 is a front view according to the third embodiment of the endoscope of the present invention, illustrating the distal end in a state in which the treatment instrument elevator base and the insulating block are attached to a rigid distal end portion.
Figure 33:
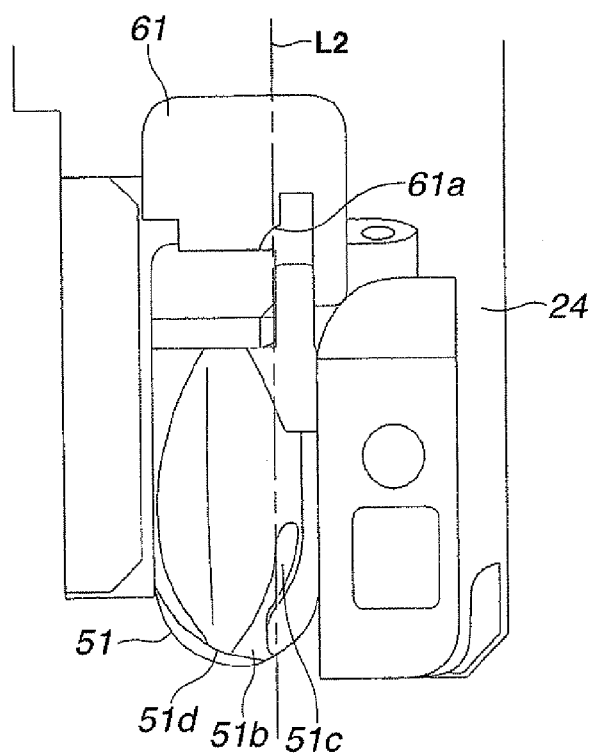
FIG. 33 is a top view according to the third embodiment of the endoscope of the present invention, illustrating the distal end in the state in which the treatment instrument elevator base and the insulating block are attached to the rigid distal end portion.

FIGS. 16 to 33 relate to the third embodiment of the endoscope of the present invention. FIG. 16 is a perspective view illustrating an external configuration of the distal end of the endoscope in a laid state of a treatment instrument elevator base. FIG. 17 is a perspective view of the distal end of the endoscope illustrated in FIG. 16, as viewed from the front side. FIG. 18 is a perspective view illustrating the external configuration of the distal end in an elevated state of the treatment instrument elevator base. FIG. 19 is a perspective view illustrating the exterior of the treatment instrument elevator base. FIG. 20 is a front view of the treatment instrument elevator base illustrated in FIG. 19. FIG. 21 is an exploded perspective view illustrating the treatment instrument elevator base and the drive arm to be attached to the treatment instrument elevator base. FIG. 22 is a perspective view illustrating the treatment instrument elevator base attached with the drive arm. FIG. 23 is a partial cross-sectional view illustrating an attached state of a rotation shaft of the drive arm to the treatment instrument elevator base. FIG. 24 is a perspective view illustrating the distal end of the endoscope, in which the drive arm is shown. FIG. 25 is a partial cross-sectional view of a modified example, illustrating an attached state of the rotation shaft of the drive arm to the treatment instrument elevator base. FIG. 26 is a cross-sectional view of a conventional example, illustrating a protection tube and a coil tube, through which an operation wire is inserted. FIG. 27 is a cross-sectional view of the protection tube and the coil tube, through which the operation wire is inserted, in a state in which the coil tube illustrated in FIG. 26 is damaged. FIG. 28 is a cross-sectional view of the present embodiment, illustrating the protection tube and the coil tube, through which the operation wire is inserted. FIG. 29 is a cross-sectional view of the protection tube and the coil tube, through which the operation wire is inserted, in a state in which the coil tube illustrated in FIG. 28 is damaged. FIG. 30 is a perspective view illustrating an insulating block. FIG. 31 is a perspective view illustrating the insulating block, as viewed in a different direction from the direction of FIG. 30. FIG. 32 is a front view of the distal end, illustrating a state in which the treatment instrument elevator base and the insulating block are attached to the rigid distal end portion. FIG. 33 is a top view of the distal end, illustrating the state in which the treatment instrument elevator base and the insulating block are attached to the rigid distal end portion.

In the following description, the components similar to the components of the first and second embodiments will be denoted by the same reference numerals, and the description thereof will be omitted. The description will be made only of components different from the components of the first and second embodiments.

As illustrated in FIGS. 16 and 17, the distal end 15 of the endoscope 1 of the present embodiment is provided with a treatment instrument elevator base 51 and an insulating block 61 which forms a contact portion. Similarly to the first embodiment, the treatment instrument elevator base 51 in the laid state is stored in the storage space 22. The treatment instrument elevator base 51 is rotated toward the insulating block 61 to be elevated, as illustrated in FIG. 18. Then, similarly to the first embodiment, the treatment instrument elevator base 51 in the elevated state sandwiches and fixes the above-described guide wire 33 or the treatment instrument such as a catheter and a high-frequency cautery instrument of a papillotomy knife, for example, together with the insulating block 61.

Similarly to the first embodiment, a surface of the treatment instrument elevator base 51 of the present embodiment is formed with a contact surface 51a which comes in contact with the guide wire 33 or the treatment instrument of a different type, as illustrated in FIGS. 19 and 20. The contact surface 51a is similar in configuration to the contact surface 23a of the first embodiment (see FIG. 4).

An upper part of the contact surface 51a is formed with a treatment instrument holding portion (hereinafter referred to as the guide wire holding portion) 51b which includes a leading surface 51d functioning as a first leading portion for guiding and leading the small-diameter guide wire 33 in accordance with the rotating movement (the elevating movement) of the treatment instrument elevator base 51 while being in contact with the guide wire 33. The guide wire holding portion 51b of the present embodiment forms a part of a treatment instrument holding mechanism, and is similar in configuration to the first leading portion 23b of the first embodiment.

The degree of tilt of the guide wire holding portion 51b or the degree of curvature (the degree R) of the curved surface is also not particularly limited, as long as the degree of tilt or the degree of curvature allows the guide wire holding portion 51b to smoothly lead and hold the small-diameter guide wire 33, with which the guide wire holding portion 51b is in contact, to a later-described guide wire fixing portion 51c.

The treatment instrument elevator base 51 of the present embodiment further includes a wall portion 52 which projects upward from a side portion, i.e., a right side portion in the drawing of FIG. 20, of the guide wire holding portion 51b formed on the surface on which the contact surface 51a is formed. The wall portion 52 forms a side surface of the guide wire holding portion 51b, and extends in the direction of the proximal end, i.e., in the direction of the later-described guide wire fixing portion 51c which forms a holding fixture portion of the treatment instrument elevator base 51.

As illustrated in FIG. 20, when the treatment instrument elevator base 51 is viewed from the front side, the wall portion 52 is disposed above and apart from the guide wire holding portion 51b by a predetermined distance to hang over the guide wire holding portion 51b and to form a substantial U-shape connected to the curved surface of the guide wire holding portion 51b for leading and holding the guide wire 33, for example. On the guide wire holding portion 51b, therefore, the wall portion 52 latches and holds the guide wire 33 led by the guide wire holding portion 51b.

On the above-described surface of the treatment instrument elevator base 51 extending from the guide wire holding portion 51b in the direction of the proximal end, the guide wire fixing portion 51c is provided consecutively to the guide wire holding portion 51b to form the holding fixture portion for sandwiching and fixing the small-diameter guide wire 33. The guide wire fixing portion 51c is formed as a part of the guide wire holding portion 51b, and is similar in configuration to the holding portion 23c of the first embodiment.

As illustrated in FIG. 19, the guide wire fixing portion 51c is formed as a grasping surface having a predetermined size required to sandwich and hold the small-diameter guide wire 33, which has a diameter not exceeding a predetermined value and is led and held by the guide wire holding portion 51b, together with the later-described insulating block 61.

The small-diameter guide wire 33 having a diameter not exceeding a predetermined value corresponds to the guide wire 33 used in a normal treatment and having a diameter in the range of from approximately 0.02 inches to approximately 0.04 inches, for example. However, the guide wire 33 is not limited to the guide wire 33 having the above diameter.

Similarly to the first embodiment, to increase the holding force for holding the treatment instrument such as the small-diameter guide wire 33 sandwiched by the guide wire fixing portion 51c, the grasping surface of the guide wire fixing portion 51c may also be formed into a circular arc shape or a substantially V-shaped groove, for example. Further, the grasping surface of the guide wire fixing portion 51c is formed to have a large contact area with the treatment instrument or the like sandwiched by the guide wire fixing portion 51c so as to increase the holding force for holding the treatment instrument or the like, irrespective of the shape of the grasping surface.

In the thus configured treatment instrument elevator base 51, as illustrated in FIG. 21, a rotation supporting portion 53 extending from a proximal portion of the treatment instrument elevator base 51 in the direction of the proximal end is drilled with a connection hole 54, in which an elevator base drive shaft 45 of the drive arm 42 is inserted. The connection hole 54 is formed into a cubic shape having rectangular holes surfaces, and is set to have substantially the same size as the size of the elevator base drive shaft 45 of the drive arm 42. Further, the connection hole 54 is drilled with a screw hole 55 which extends from one of the sides of the connection hole 54 in an approximate center toward the corresponding side surface of the rotation supporting portion 53 in the direction of a diagonal of the hole surfaces (at approximately 45 degrees with respect to the side forming the hole surfaces).

A fixing screw 56 is screwed into the screw hole 55 to fix the elevator base drive shaft 45 in the connection hole 54 of the rotation supporting portion 53. Thereby, as illustrated in FIG. 22, the drive arm 42 is connected and fixed to the rotation supporting portion 53 of the treatment instrument elevator base 51. The drive arm 42 is provided with a flange portion 46 which comes in contact with a surface of the rotation supporting portion 53, when the elevator base drive shaft 45 is attached to the treatment instrument elevator base 51, to control the position of the elevator base drive shaft 45.

In the present embodiment, as illustrated in FIG. 23, the fixing screw 56 abuts against the corner of one of the sides of the elevator base drive shaft 45, i.e., the diagonally lower left corner in the drawing in the present example, to fixedly hold the elevator base drive shaft 45 in the connection hole 54 of the rotation supporting portion 53. In the above state, two surfaces of the elevator base drive shaft 45 forming the corner in the circular broken line a shown in FIG. 23, i.e., the diagonally upper right corner in the drawing in the present example, abut against two surfaces of the rotation supporting portion 53 forming the connection hole 54.

Therefore, the rotation supporting portion 53 of the treatment instrument elevator base 51 and the elevator base drive shaft 45 are reliably fixed to each other, and the rattling arising from the attachment of the components can be prevented. Accordingly, the fixing force for fixing the treatment instrument elevator base 51 and the drive arm 42 can be ensured, and a stable operation of adjusting the elevation angle of the treatment instrument elevator base 51 can be constantly performed.

As illustrated in FIG. 24, similarly to the second embodiment, the drive arm 42 is stored in the concave portion 40, which is recessed from the outer circumference of the distal end 15 into the concave shape. As the operation wire 36 is pulled and slacked, the drive arm 42 is rotated to bring the treatment instrument elevator base 51 into the elevated state and the laid state.

A contact surface of the fixing screw 56, which comes in contact with the elevator base drive shaft 45, may be formed into a tilted surface so that the fastened fixing screw 56 causes the above-described two surfaces of the elevator base drive shaft 45 forming the above-described corner to reliably abut against the above-described two surfaces forming the connection hole 54.

Further, as illustrated in FIG. 25, the elevator base drive shaft 45 may include a contact surface 45a, which is a planarized portion of the elevator base drive shaft 45 to be in contact with the fixing screw 56. The above configuration ensures the contact between the fixing screw 56 and the elevator base drive shaft 45, and the fixing force for fixing the treatment instrument elevator base 51 and the drive arm 42 can be further ensured. Further, since the direction of attaching the elevator base drive shaft 45 in the connection hole 54 is regulated in the attachment process, the drive arm 42 can be prevented from being inappropriately attached to the treatment instrument elevator base 51.

Meanwhile, the operation wire 36, which is pulled and slacked to bring the treatment instrument elevator base 51 into the elevated state and the laid state via the drive arm 42, is covered by a two-layer protection tube formed by a coil tube and a Teflon (registered trademark) tube from inside of the insertion portion 10 to the operation portion 11 of the endoscope 1. The Teflon (registered trademark) tube covers the operation wire 36 as the outermost cladding member to prevent, in the event of damage to the coil tube for some reason, a bending portion rubber forming the cladding of the bending portion 14, for example, from being damaged from a damaged section of the coil tube.

As illustrated in FIG. 26, according to a conventional structure, a protection tube 37 forming the Teflon (registered trademark) tube and a coil tube 38 formed of metal are not in close contact with each other, and thus a gap S is formed. Therefore, if the coil tube 38 is damaged (e.g., cut) for some reason, the damaged section of a damaged part B as illustrated in FIG. 27 may damage the inner surface of the protection tube 37, while moving back and forth or vertically vibrating with respect to the protection tube 37 through the bending operation of the bending portion 14. Further, the damaged part B may eventually break through the protection tube 37 and damage the bending portion rubber of the bending portion 14.

As illustrated in FIG. 28, the present embodiment is structured such that the protection tube 37 and the coil tube 38 are made in close contact with each other. The protection tube 37 is a heat shrinkable tube, and is made in close contact with the outer circumference of the coil tube 38 by heat treatment.

With the above configuration, if the coil tube 38 is damaged (e.g., cut) for some reason, as illustrated in FIG. 29, the protection tube 37 is constantly in close contact with the outer circumference of the coil tube 38 even during the bending operation of the bending portion 14, and thus free movement of the coil tube 38 is prevented. Therefore, the inner surface of the protection tube 37 is prevented from being damaged by the damaged section of the damaged part B.

As a result, the damaged part B of the coil tube 38 is prevented from breaking through the protection tube 37 and damaging the bending portion rubber of the bending portion 14.

The insulating block 61 of the present embodiment will now be described with reference to FIGS. 30 and 31.

The insulating block 61 of the present embodiment corresponds to the contact portion 34 of the first embodiment, and includes a guide wire holding fixture portion 61*a* which fixes the small-diameter guide wire 33, a guide wire leading portion 61*b* which is a curved and tilted surface for leading the small-diameter guide wire 33 to the guide wire holding fixture portion 61*a*, a release groove 61*c* in which an edge portion of the contact surface 51*a* of the treatment instrument elevator base 51 is inserted, and a wall portion release groove 61*d* in which the wall portion 52 of the treatment instrument elevator base 51 is inserted.

The guide wire holding fixture portion Ma is a contact surface, with which the small-diameter guide wire 33 comes in contact, and which is formed by chamfering a corner on the side of the wall portion release groove 61*d* into a curved surface. Further, the guide wire leading portion 61*b* is formed by further chamfering the corner on the side of the wall portion release groove 61*d* from the lower side of the corner into a more curved surface than the guide wire holding fixture portion 61*a*.

The reference numeral 62 denotes a holding fixture portion for the large-diameter treatment instrument, which is the same in configuration, operation, and effect as the holding fixture portion of the first embodiment. Thus, detailed description of the holding fixture portion 62 will be omitted.

The thus configured treatment instrument elevator base 51 and insulating block 61 of the present embodiment are attached to the rigid distal end portion 24 of the distal end 15 in, a similar manner to the first embodiment, as illustrated in FIGS. 32 and 33.

In the attached state, the guide wire fixing portion 51*c* of the treatment instrument elevator base 51 and the guide wire holding fixture portion 61*a* of the insulating block 61 are disposed on substantially the same straight line. Specifically, the alternate long and short dashed lines L1 and L2 shown in FIGS. 32 and 33 indicate the plane passed by the locus defined by the movement of the guide wire fixing portion 51*c* when the treatment instrument elevator base 51 is elevated in accordance with the rotation thereof.

The guide wire fixing portion 51*c* of the treatment instrument elevator base 51 and the guide wire holding fixture portion 61*a* of the insulating block 61 are located in the plane including both of the alternate long and short dashed lines L1 and L2. That is, the guide wire holding fixture portion 61*a* of the insulating block 61 is located in the plane including the locus plane defined by the movement of the guide wire fixing portion 51*c* of the treatment instrument elevator base 51.

Accordingly, in accordance with the elevating movement of the treatment instrument elevator base 51, the small-diameter guide wire 33 held by the guide wire fixing portion 51*c* of the treatment instrument elevator base 51 is moved within the plane to be effectively led to the guide wire holding fixture portion 61*a* of the insulating block 61, and is reliably sandwiched and fixed by the treatment instrument elevator base 51 and the insulating block 61.

The operation of the endoscope 1 of the present embodiment will now be described with reference to FIGS. 34 to 45.

Figure 34:
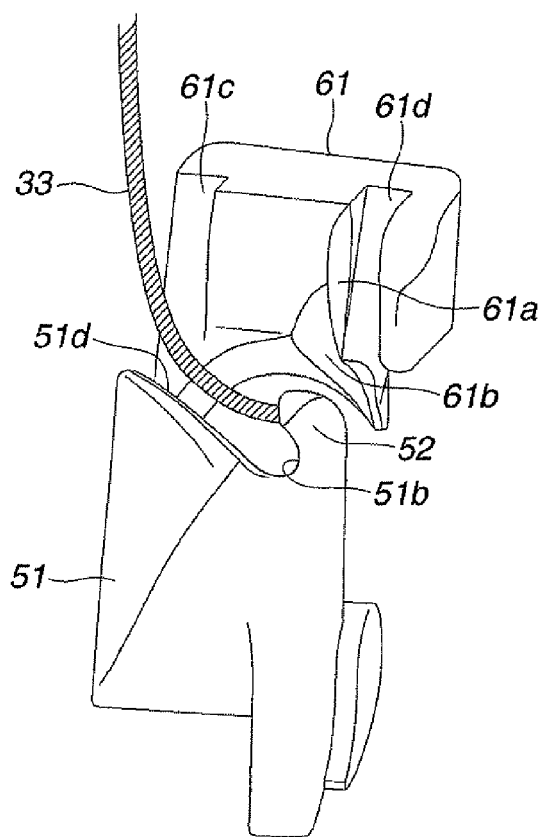
FIG. 34 is a diagram for explaining the operation of the third embodiment, illustrating a state prior to the elevating movement of the treatment instrument elevator base, in which the guide wire is inserted in the distal end body.
Figure 35:
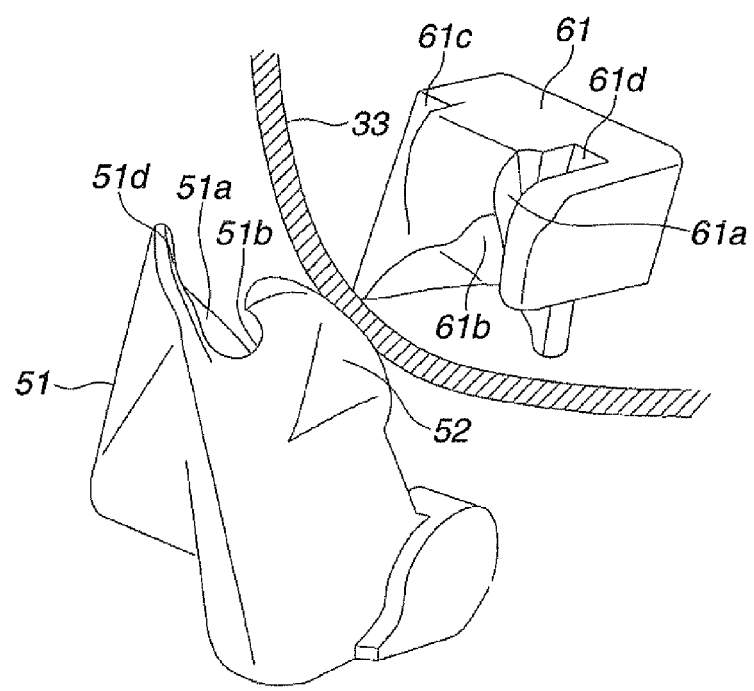
FIG. 35 is a diagram for explaining the operation of the third embodiment, illustrating the state prior to the elevating movement of the treatment instrument elevator base, as viewed in a different angle from the angle of FIG. 34.
Figure 36:
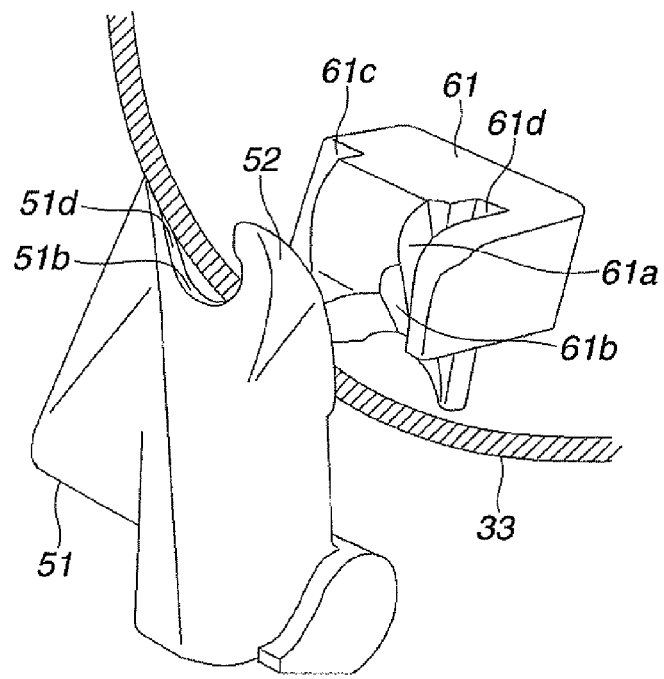
FIG. 36 is a diagram for explaining the operation of the third embodiment, illustrating an initial state in which the guide wire is led by a leading surface of the treatment instrument elevator base toward a treatment instrument holding portion.
Figure 37:
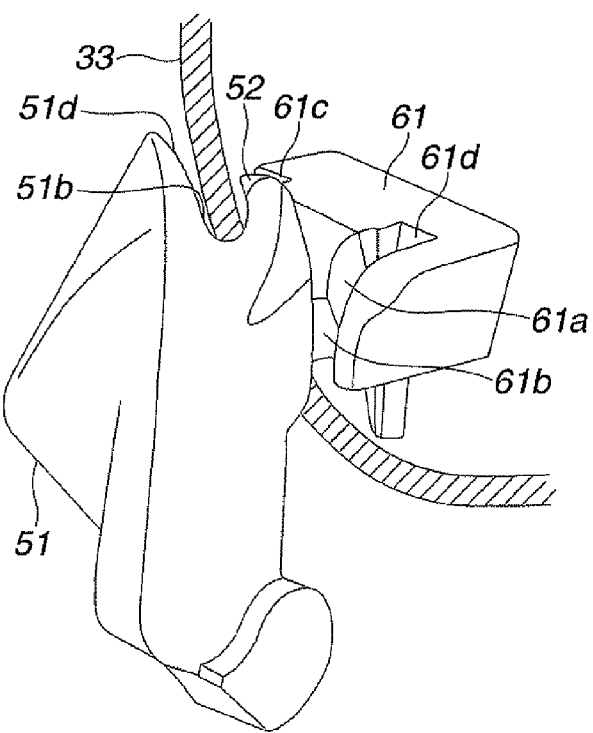
FIG. 37 is a diagram for explaining the operation of the third embodiment, illustrating a state in which the treatment instrument elevator base is further elevated and the guide wire is led to the treatment instrument holding portion.
Figure 38:
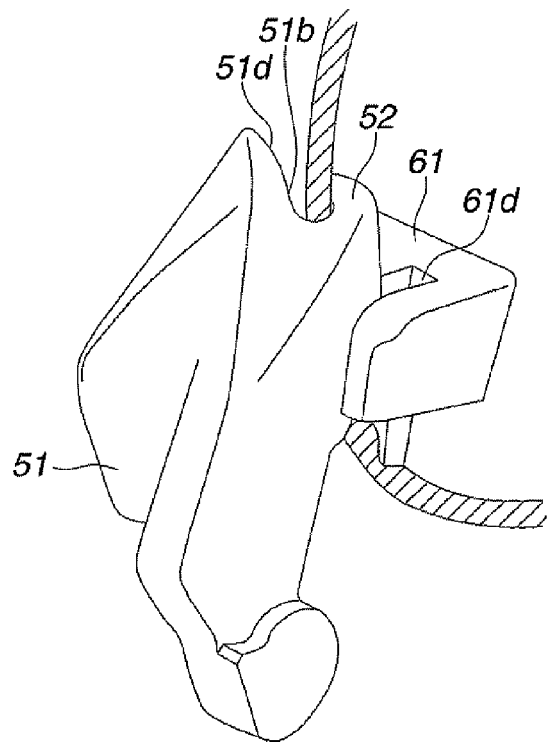
FIG. 38 is a diagram for explaining the operation of the third embodiment, illustrating a state in which a wall portion of the further elevated treatment instrument elevator base is set in a wall portion release groove of the insulating block.
Figure 39:
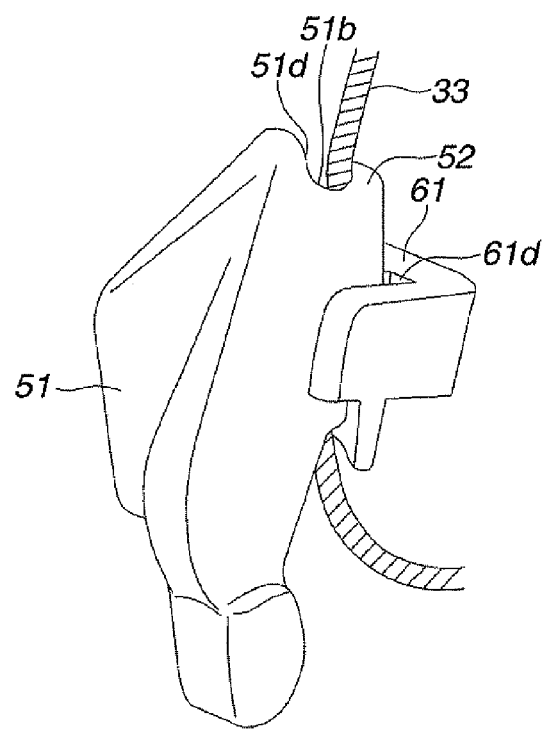
FIG. 39 is a diagram for explaining the operation of the third embodiment, illustrating a state in which the guide wire is sandwiched and fixed by the treatment instrument elevator base and the insulating block.
Figure 40:
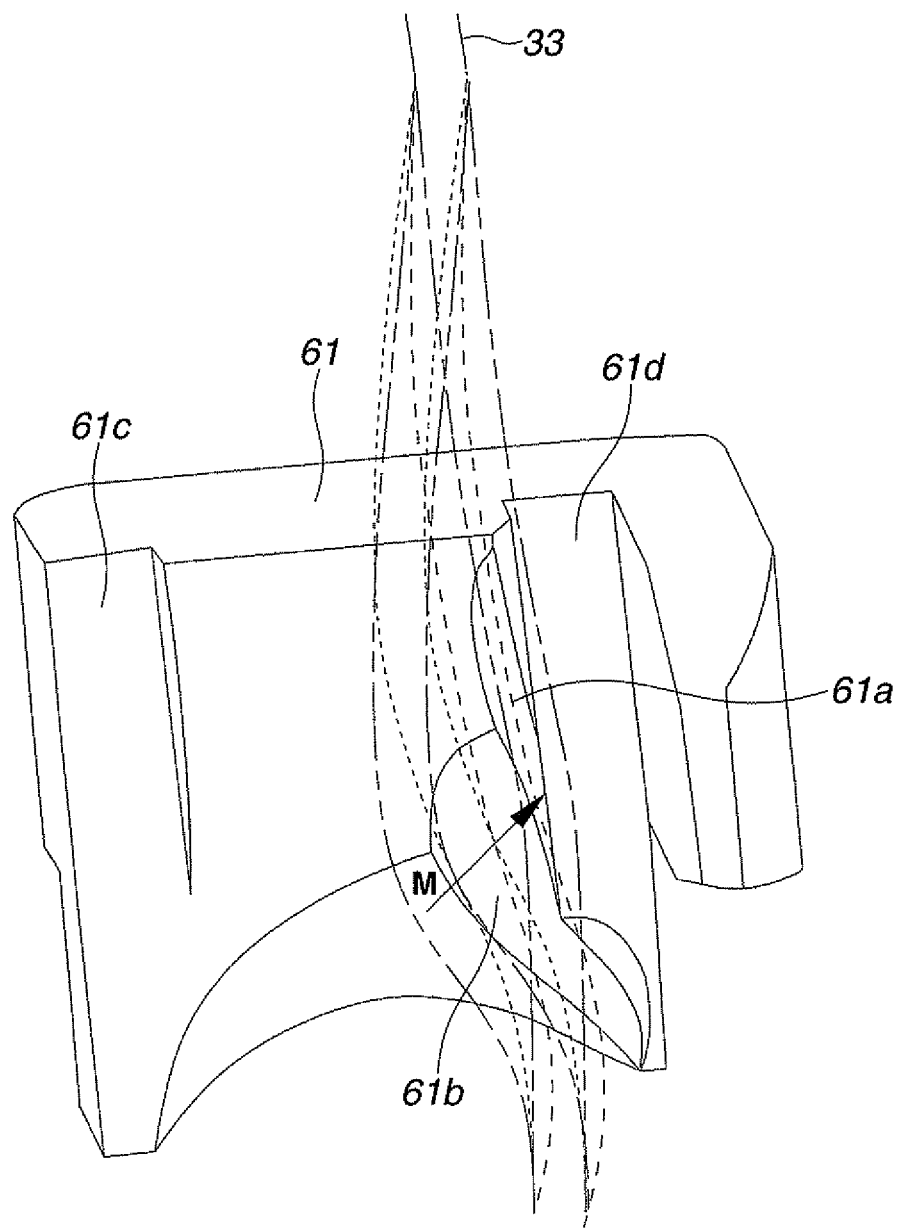
FIG. 40 is a diagram for explaining the operation of the third embodiment, illustrating a state in which the guide wire is led by a guide wire leading portion of the insulating block.
Figure 41:
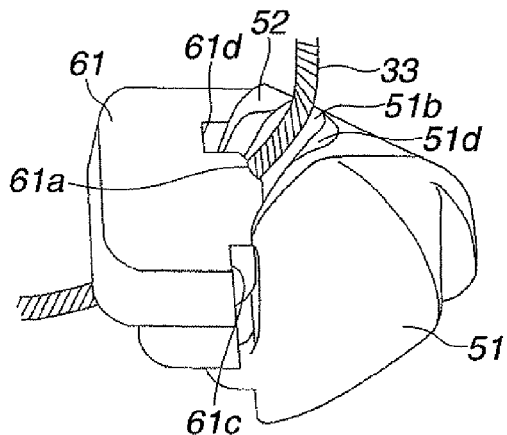
FIG. 41 is a diagram for explaining the operation of the third embodiment, illustrating the state in which the guide wire is sandwiched and fixed by the treatment instrument elevator base and the insulating block, as viewed in a different angle from the angle of FIG. 39.
Figure 42:
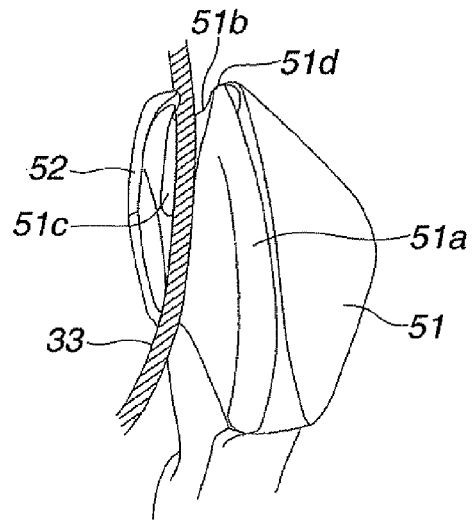
FIG. 42 is a diagram for explaining the operation of the third embodiment, illustrating only the treatment instrument elevator base and the guide wire in the state in which the guide wire is sandwiched and fixed by the treatment instrument elevator base and the insulating block.
Figure 43:
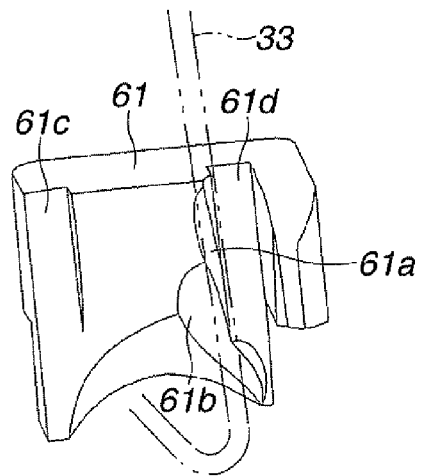
FIG. 43 is a diagram for explaining the operation of the third embodiment, illustrating only the insulating block and the guide wire in the state in which the guide wire is sandwiched and fixed by the treatment instrument elevator base and the insulating block.
Figure 44:
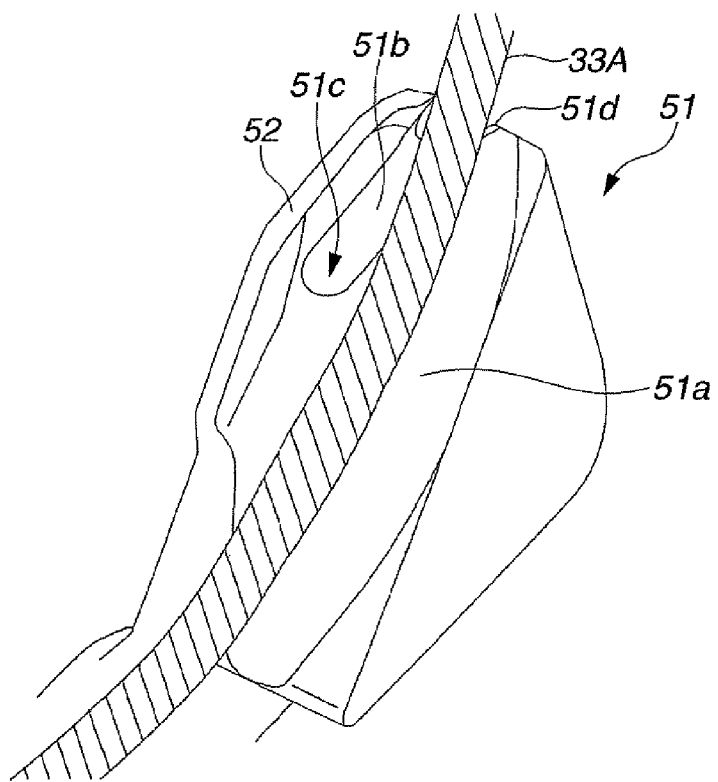
FIG. 44 is a diagram for explaining the operation of the third embodiment, and for explaining the treatment instrument elevator base in elevating the large-diameter treatment instrument.
Figure 45:
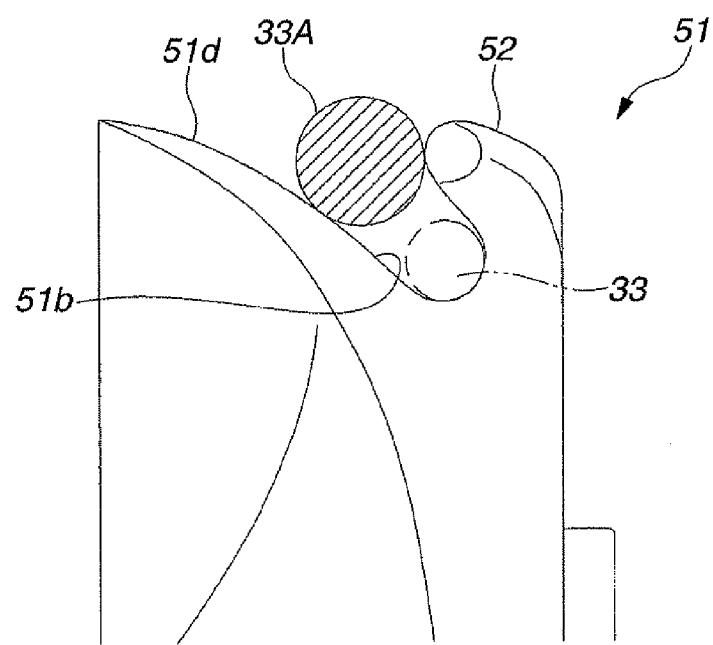
FIG. 45 is a front view of the treatment instrument elevator base illustrated in FIG. 44 for explaining the operation of the third embodiment.

FIGS. 34 to 42 are perspective views for explaining the operation of the third embodiment, and illustrate the treatment instrument elevator base, the insulating block, and the small-diameter guide wire in accordance with respective steps. FIG. 34 is a diagram illustrating a state prior to the elevating movement of the treatment instrument elevator base, in which the guide wire is inserted in the distal end body. FIG. 35 is a diagram illustrating the state prior to the elevating movement of the treatment instrument elevator base, as viewed in a different angle from the angle of FIG. 34. FIG. 36 is a diagram illustrating an initial state in which the guide wire is led by the leading surface of the treatment instrument elevator base toward the treatment instrument holding portion. FIG. 37 is a diagram illustrating a state in which the treatment instrument elevator base is further elevated and the guide wire is led to the treatment instrument holding portion. FIG. 38 is a diagram illustrating a state in which the wall portion of the further elevated treatment instrument elevator base is set in the wall portion release groove of the insulating block. FIG. 39 is a diagram illustrating a state in which the guide wire is sandwiched and fixed by the treatment instrument elevator base and the insulating block. FIG. 40 is a diagram illustrating a state in which the guide wire is led by the guide wire leading portion of the insulating block. FIG. 41 is a diagram illustrating the state in which the guide wire is sandwiched and fixed by the treatment instrument elevator base and the insulating block, as viewed in a different angle from the angle of FIG. 39. FIG. 42 is a diagram illustrating only the treatment instrument elevator base and the guide wire in the state in which the guide wire is sandwiched and fixed by the treatment instrument elevator base and the insulating block. FIG. 43 is a diagram illustrating only the insulating block and the guide wire in the state in which the guide wire is sandwiched and fixed by the treatment instrument elevator base and the insulating block. FIG. 44 is a diagram for explaining the treatment instrument elevator base in elevating the large-diameter treatment instrument. FIG. 45 is a front view of the treatment instrument elevator base illustrated in FIG. 44.

It is assumed in the following description that a surgeon performs observation or treatment of the pancreaticobiliary ducts by using the endoscope 1 in a similar manner to the first embodiment. The following description will be limited to the operation in which the guide wire 33 is sandwiched by the treatment instrument elevator base 51 and the insulating block 61 of the present embodiment. Other operations of the present embodiment are similar to the operations of the first embodiment.

In a similar manner to the first embodiment, the surgeon transpapillarily inserts the guide catheter into a pancreatic duct or a bile duct (not illustrated), and inserts the guide wire 33 from the cap provided on the proximal end side of the guide catheter. Then, the surgeon confirms under X-ray illumination that the distal end of the guide wire 33 has been inserted inside the pancreatic duct or the bile duct, and grasps by hand the proximal end side of the guide wire 33.

Subsequently, the surgeon performs the operation of withdrawing the guide catheter. The surgeon confirms from an observed image that the guide catheter has been withdrawn from the papilla, and thereafter withdraws the guide catheter further toward the proximal side. Then, the surgeon operates the elevating operation knob 16 of the operation portion 11.

As the elevating operation knob 16 of the operation portion 11 is operated, the treatment instrument elevator base 51 in the laid state, as illustrated in FIGS. 34 and 35, starts to be elevated. Then, in accordance with the elevation of the treatment instrument elevator base 51, the guide wire 33 comes in contact with the leading surface 51d illustrated in FIG. 35 due to the reaction force thereof, and is led toward the guide wire holding portion 51b, as illustrated in FIG. 36.

As the treatment instrument elevator base 51 is further elevated, the guide wire 33 is held by the guide wire holding portion 51b, being latched by the wall portion 52 which forms a side surface of the guide wire holding portion 51b. As illustrated in FIG. 37, the treatment instrument elevator base 51 is rotated toward the insulating block 61 and further elevated, while keeping the guide wire 33 latched and held on the guide wire holding portion 51b by the wall portion 52. In the above process, the guide wire 33 exerts the reaction force to keep the linear shape thereof. Thus, the guide wire 33 is pressed into the guide wire fixing portion 51c of the treatment instrument elevator base 51 to be firmly locked therein.

Then, in the further elevated treatment instrument elevator base 51, the wall portion 52 is set in the wall portion release groove 61d of the insulating block 61, as illustrated in FIGS. 38 and 39. In the above state, as illustrated in FIG. 40, while being held by the guide wire holding portion 51b, the guide wire 33 comes in contact with the leading surface which forms a surface of the guide wire leading portion 61b of the insulating block 61, and is guided and led to the guide wire holding fixture portion 61a (in the direction of the arrow M shown in the figure).

Then, as illustrated in FIGS. 39 and 41 to 43, the guide wire 33 is firmly sandwiched by the guide wire fixing portion 51c of the treatment instrument elevator base 51 and the guide wire holding fixture portion 61a of the insulating block 61.

Meanwhile, as illustrated in FIG. 44, the large-diameter treatment instrument 33A including the treatment instrument such as a catheter is led toward the guide wire fixing portion 51c by the guide wire holding portion 51b of the contact surface 51a of the treatment instrument elevator base 51. However, the large-diameter treatment instrument 33A comes in contact with the wall portion 52, and is prevented from being set in the guide wire fixing portion 51c. Thus, the large-diameter treatment instrument 33A is not held by the guide wire fixing portion 51c. That is, as illustrated in FIG. 45, while the guide wire 33 is led to the guide wire holding portion 51b and latched and held by the wall portion 52 of the treatment instrument elevator base 51 at a first position in the guide wire fixing portion 51c, the large-diameter treatment instrument 33A is prevented by the wall portion 52 from being set in the guide wire fixing portion 51c and is caught on the contact surface 51a to be held at a second position.

In other words, the treatment instrument elevator base 51 is elevated to cause the guide wire holding portion 51b, which is formed on the contact surface 51a to come in contact with and hold the guide wire 33 or the large-diameter treatment instrument 33A of a different type, to lead the guide wire 33 to the first position of the guide wire fixing portion 51c, or to come in contact with and hold the large-diameter treatment instrument 33A having a diameter equal to or greater than a predetermined value at the second position on the contact surface 51a. That is, the guide wire holding portion 51b forms an elevator-base-side leading portion for leading the guide wire 33 or the large-diameter treatment instrument 33A of a different type in accordance with the elevation of the treatment instrument elevator base 51.

That is, in the present embodiment, the size of the wall portion 52 of the treatment instrument elevator base 51 is set to prevent the large-diameter treatment instrument 33A including the treatment instrument such as a catheter, which has a diameter equal to or greater than 0.04 inches, for example, from being set in the guide wire holding portion 51b. The operation of holding and fixing the large-diameter treatment instrument 33A in the elevated state of the treatment instrument elevator base 51 is similar to the operation of the first embodiment. Thus, the description thereof will be omitted.

As described above, the endoscope 1 of the present embodiment exerts similar effects to the effects of the first embodiment. In addition, in the endoscope 1 of the present embodiment, the treatment instrument elevator base 51 is provided with the wall portion 52 which forms the side wall of the guide wire holding portion 51b. Thus, the endoscope 1 of the present embodiment can minimize the occurrence of unnecessary movement, such as lateral sway of the guide wire 33 or the large-diameter treatment instrument 33A, when the treatment instrument elevator base 51 is elevated while keeping the guide wire 33 or the large-diameter treatment instrument 33A latched. Accordingly, it is possible to prevent, for the benefit of the surgeon, the deterioration of the operability and the visibility caused by the unnecessary movement of the guide wire 33 or the large-diameter treatment instrument 33A appearing on the screen of the monitor 4, and to reduce uncomfortable feeling arising from the image.

The invention described in the above embodiments is not limited to the embodiments and the modified examples thereof, but various modifications can be made in the phase of practicing the present invention within a scope not departing from the gist of the invention. Further, the embodiments include the invention at various stages, and various inventions can be extracted by appropriately combining a plurality of disclosed constituent elements.

For example, even if some constituent elements are eliminated from all constituent elements described in the embodiments, such an arrangement with the elimination of the constituent elements can be extracted as an invention, as long as the object of the present invention described in the section of Background of the Invention can be achieved and the effects described in the section of the Detailed Description of the Invention can be obtained.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
an insertion portion including a distal end on a distal end side thereof and inserted into a body cavity;
a treatment instrument insertion channel disposed in the insertion portion and communicating with the distal end;
a treatment instrument elevator base rotatably provided at the distal end to elevate a treatment instrument inserted into the treatment instrument insertion channel in accordance with an operation of an operation portion, the treatment instrument including a large-diameter treatment instrument having a radius exceeding a predetermined value and a small-diameter treatment instrument having a radius not exceeding the predetermined value;
a contact portion provided at the distal end, the contact portion being configured to be opposed to the treatment instrument elevator base and to hold and fix the treatment instrument by sandwiching the treatment instrument together with the treatment instrument elevator base when the treatment instrument elevator base is elevated;
a contact surface formed on the treatment instrument elevator base, the contact surface being configured to come in contact with the treatment instrument when the treatment instrument elevator base is elevated, and to hold and fix the large-diameter treatment instrument by sandwiching the large-diameter treatment instrument together with the contact portion;
a holding portion formed on the treatment instrument elevator base, the holding portion being configured to hold and fix the small-diameter treatment instrument thinner than the large-diameter treatment instrument by sandwiching the small-diameter treatment instrument together with the contact portion;
a first leading portion provided between the contact surface and the holding portion of the treatment instrument elevator base, the first leading portion being configured to lead the treatment instrument from the contact surface to the holding portion while being in contact with the treatment instrument in accordance with a rotating movement of the treatment instrument elevator base;
a first holding fixture portion provided at the contact portion and including a grasping surface of a predetermined width smaller than the radius of the large-diameter treatment instrument, the first holding fixture portion being configured to be opposed to the holding portion in a state where the treatment instrument elevator base is elevated and to hold and fix the small-diameter treatment instrument having the radius not exceeding the predetermined value which is led by the first leading portion by sandwiching the small-diameter treatment instrument together with the holding portion;
a second holding fixture portion provided at the contact portion, the second holding fixture portion being configured to be opposed to the contact surface in the state where the treatment instrument elevator base is elevated and to hold and fix the large-diameter treatment instrument having the radius exceeding the predetermined value by sandwiching the large-diameter treatment instrument together with the contact surface; and
a second leading portion provided between the first holding fixture portion and the second holding fixture portion of the contact portion, the second leading portion being configured to lead the large-diameter treatment instrument which has the radius exceeding the predetermined width of the grasping surface of the first holding fixture portion from the first holding fixture portion to the second holding fixture portion for sandwiching the large-diameter treatment instrument together with the contact surface on the treatment instrument elevator base in accordance with the elevation of the treatment instrument elevator base.

2. The endoscope according to claim 1,
wherein the first leading portion is configured to form a tilted surface or a curved surface for leading the treatment instrument to an edge portion of the contact surface of the treatment instrument elevator base.

3. The endoscope according to claim 2,
wherein the first holding fixture portion is configured such that the grasping surface is disposed at an edge portion of the contact portion when the treatment instrument elevator base is elevated.

4. The endoscope according to claim 1,
wherein the second leading portion is configured to form a tilted surface or a curved surface for leading the large-diameter treatment instrument to a predetermined fixing position.

5. The endoscope according to claim 1,
wherein the small-diameter treatment instrument is a guide wire.

6. The endoscope according to claim 5,
wherein the guide wire has a diameter in the range of from 0.02 inches to 0.04 inches.

* * * * *